US008545884B2

(12) United States Patent
Messerschmid et al.

(10) Patent No.: US 8,545,884 B2
(45) Date of Patent: Oct. 1, 2013

(54) SOLID PHARMACEUTICAL FORMULATIONS COMPRISING BIBW 2992

(75) Inventors: Roman Messerschmid, Biberach (DE); Thomas Friedl, Ochsenhausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 197 days.

(21) Appl. No.: 12/995,715

(22) PCT Filed: Jun. 5, 2009

(86) PCT No.: PCT/EP2009/056944
§ 371 (c)(1),
(2), (4) Date: Jan. 7, 2011

(87) PCT Pub. No.: WO2009/147238
PCT Pub. Date: Dec. 10, 2009

(65) Prior Publication Data
US 2011/0142929 A1    Jun. 16, 2011

(30) Foreign Application Priority Data

Jun. 6, 2008 (EP) .................................. 08157800
May 14, 2009 (EP) .................................. 09160297

(51) Int. Cl.
*A61K 31/517* (2006.01)
*A61K 9/14* (2006.01)
*A61K 9/28* (2006.01)
*A61P 11/00* (2006.01)
*A61P 1/00* (2006.01)
*B29C 43/08* (2006.01)

(52) U.S. Cl.
USPC ...... 424/465; 424/489; 424/474; 514/266.24; 264/109

(58) Field of Classification Search
USPC .................... 424/465, 489, 474; 514/266.24; 264/109
See application file for complete search history.

(56) References Cited

U.S. PATENT DOCUMENTS 7,019,012 B2    3/2006    Himmelsbach et al.
7,220,750 B2    5/2007    Himmelsbach et al.
(Continued)

FOREIGN PATENT DOCUMENTS

WO    0078735 A1    12/2000
WO    0250043 A1    6/2002
(Continued)

OTHER PUBLICATIONS

Sune Negre, J. M. "New Galenic Contributions to Administration Forms". Continued Training for Hospital Pharmacists 3.2. http://www.ub.es/legmh/capitols/sunyenegre.pdf, Downloaded from the internet Feb. 23, 2011 per IDS filed Apr. 23, 2012.

(Continued)

*Primary Examiner* — Aradhana Sasan
(74) *Attorney, Agent, or Firm* — Michael P. Morris; Anthony P. Bottino

(57) ABSTRACT

The present invention relates to a pharmaceutical dosage form containing the active substance BIBW 2992 as the dimaleate salt, providing an immediate release profile of the active substance, further, the invention relates to compacted intermediates comprising BIBW 2992 dimaleate salt (BIBW 2992 MA$_2$) in form of a powder prepared using a combined roller compaction and sieving step from BIBW 2992 MA$_2$, intermediate blends prepared from said compacted intermediate as well as solid oral formulations providing an immediate release profile of the active substance, made from said compacted intermediate or from said intermediate blends ready for use/ingestion, e.g. capsule and tablet formulations such as uncoated or film-coated tablets prepared by direct-compression, and methods for their production.

20 Claims, 10 Drawing Sheets

Compaction Process to the "BIBW 2992 MA$_2$ compacted intermediate"

Ref 1: Precipitated BIBW 2992 salt
Ref 2: Compaction rolls
Ref 3: Ribbon
Ref 4: Granulator unit
Ref 5: Broken-up ribbon
Ref 6: Sieving machine
Ref 7: BBW 2992 compacted intermediate

(56) References Cited

U.S. PATENT DOCUMENTS

| | | |
|---|---|---|
| 7,846,936 B2 | 12/2010 | Hilberg et al. |
| 7,960,546 B2 | 6/2011 | Schroeder et al. |
| 8,067,593 B2 | 11/2011 | Schroeder et al. |
| RE43,431 E | 5/2012 | Himmelsbach et al. |
| 8,188,274 B2 | 5/2012 | Schroeder et al. |
| 2002/0169180 A1 | 11/2002 | Himmelsbach et al. |
| 2002/0173509 A1 | 11/2002 | Himmelsbach et al. |
| 2003/0225079 A1 | 12/2003 | Singer et al. |
| 2005/0043233 A1 | 2/2005 | Stefanic et al. |
| 2005/0085495 A1 | 4/2005 | Soyka et al. |
| 2006/0058311 A1 | 3/2006 | Munzert et al. |
| 2006/0100223 A1 | 5/2006 | Himmelsbach et al. |
| 2007/0027170 A1 | 2/2007 | Soyka et al. |
| 2007/0099918 A1 | 5/2007 | Singer et al. |
| 2007/0185091 A1 | 8/2007 | Himmelsbach et al. |
| 2007/0281934 A1* | 12/2007 | Buggy et al. ............ 514/235.2 |
| 2008/0254040 A1 | 10/2008 | Stefanic et al. |
| 2009/0238828 A1 | 9/2009 | Munzert et al. |
| 2009/0306044 A1 | 12/2009 | Solca et al. |
| 2009/0306101 A1 | 12/2009 | Solca et al. |
| 2009/0306378 A1 | 12/2009 | Schroeder et al. |
| 2009/0318480 A1 | 12/2009 | Solca |
| 2010/0010023 A1 | 1/2010 | Himmelsbach et al. |
| 2010/0069414 A1 | 3/2010 | Himmelsbach et al. |
| 2010/0144639 A1 | 6/2010 | Singer et al. |
| 2011/0039863 A1 | 2/2011 | Hilberg et al. |
| 2011/0046168 A1 | 2/2011 | Himmelsbach et al. |
| 2011/0142929 A1 | 6/2011 | Messerschmid et al. |
| 2011/0171289 A1 | 7/2011 | Stefanic et al. |
| 2011/0207929 A1 | 8/2011 | Schroeder et al. |
| 2011/0207932 A1 | 8/2011 | Schroeder et al. |
| 2012/0107399 A1 | 5/2012 | Barta |
| 2012/0157472 A1 | 6/2012 | Larsen et al. |

FOREIGN PATENT DOCUMENTS

| | | |
|---|---|---|
| WO | 03094921 A2 | 11/2003 |
| WO | 2004096224 A2 | 11/2004 |
| WO | 2005037824 A2 | 4/2005 |
| WO | 2006018182 A1 | 2/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |
| WO | 2009147238 A1 | 12/2009 |
| WO | 2010081817 A1 | 7/2010 |
| WO | 2011003853 A2 | 1/2011 |
| WO | 2011069962 A1 | 6/2011 |

OTHER PUBLICATIONS

Eskens, F. et al., "A phase I does escalation study of BIBW2992, an erreversible dual inhibitor of epidermal growth factor receptor I (EGFR) and 2 (HR2) tyrosine kinase in a 2-week on, 2-week off schedule in patients with advanced solid tumors". British Journal of Cancer, 2008, 98, p. 80-85.

International Search Report for PCT/EP2009/056944 mailed Sep. 7, 2009.

Sune Negre, J. M. "New Galenic Contributions to Administration Forms". Continued Training for Hospital Pharmacists 3.2. [downloaded from the internet Feb. 23, 2011]http://www.ub.es/legmh/capitols/sunyenegre.pdf.

Podczeck, F. et al., "The influence of particle size and shape on the angle of internal friction and the flow factor of unlubricated and lubricated powders". International Journal of Pharmaceutics, vol. 144, No. 2, 1996, pp. 187-194.

Herting, M.G. et al., "Roll compaction/dry granulation: Effect of raw material particle size on granule and table properties." International Journal of Pharmaceuticals, vol. 338, No. 1-2, 2007, pp. 110-118.

* cited by examiner

Figure 1: Compaction Process to the "BIBW 2992 MA$_2$ compacted intermediate"
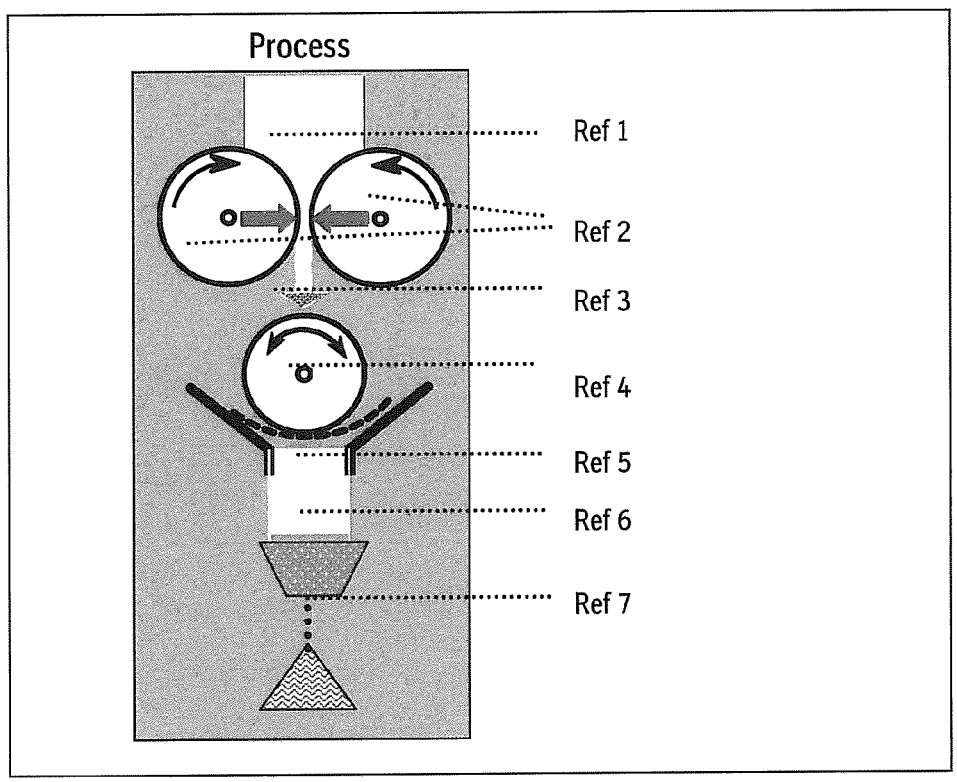
Ref 1: Precipitated BIBW 2992 salt
Ref 2: Compaction rolls
Ref 3: Ribbon
Ref 4: Granulator unit
Ref 5: Broken-up ribbon
Ref 6: Sieving machine
Ref 7: BBW 2992 compacted intermediate Figure 2: Acceleration of Disintegration Time (20mg Tablets) by increased Roller Compaction Force
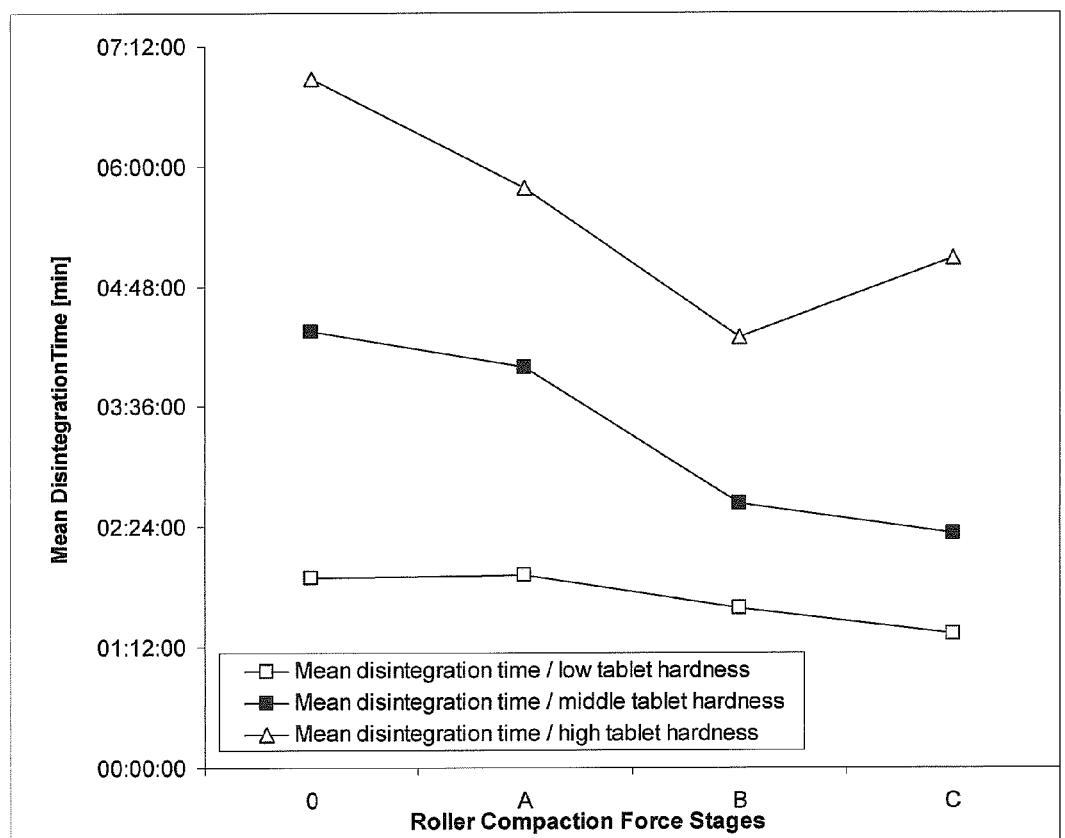
Roller Compaction Stages:   0 = No Pre-compaction of API
                             A → C = Increasing Compaction Force Figure 3: Acceleration of Dissolution Rate (20mg Tablets) by increased Roller Compaction Force
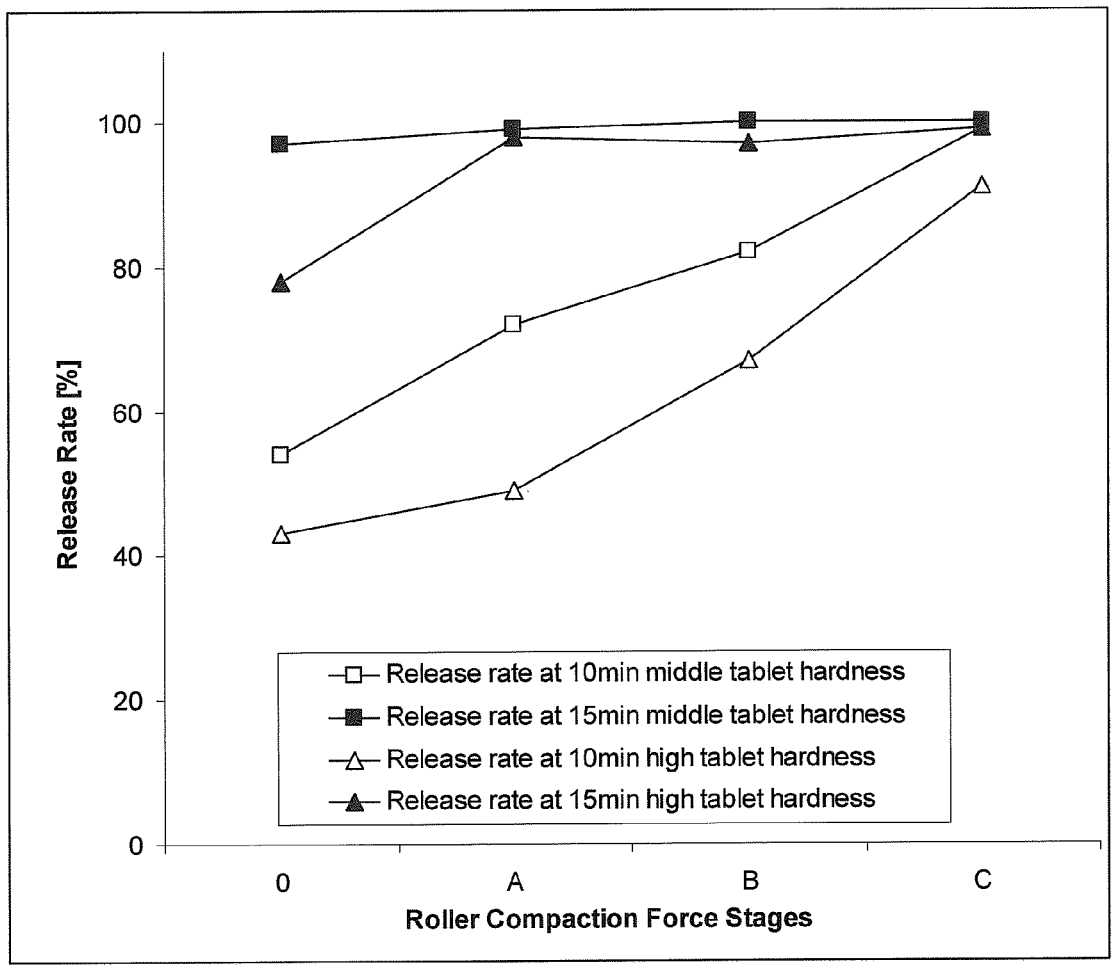
Roller Compaction Stages: 0 = No Pre-compaction of API
A → C = Increasing Compaction Force Figure 4: Optical Particle Size Analysis of Precipitated BIBW 2992 MA$_2$ and Compacted Intermediates produced thereof by variation of Compaction Force (Instrument: Occhio 500 Pharma, Particle Metrix GmbH)
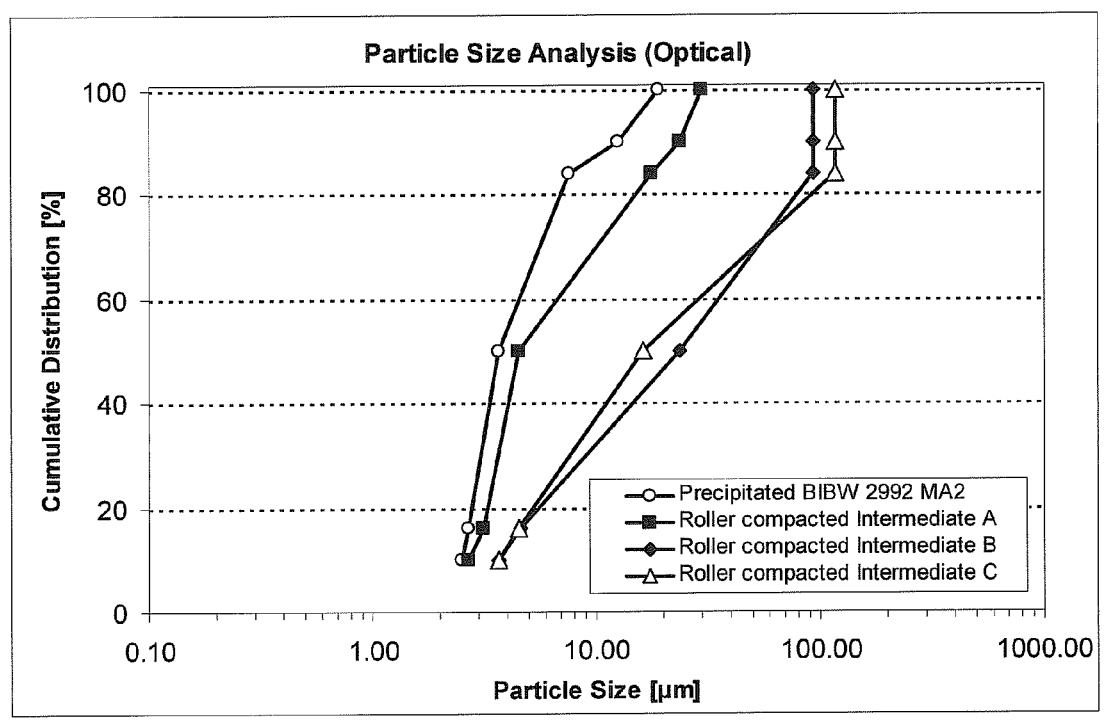
Roller Compaction Stages: A → C = Increasing Compaction Force Figure 5: Laser Diffraction Particle Size Analysis of Precipitated BIBW 2992 $MA_2$ and Compacted Intermediates produced thereof by variation of Compaction Force (Instrument: Helos KF with RODOS dispersion, Sympatec GmbH)
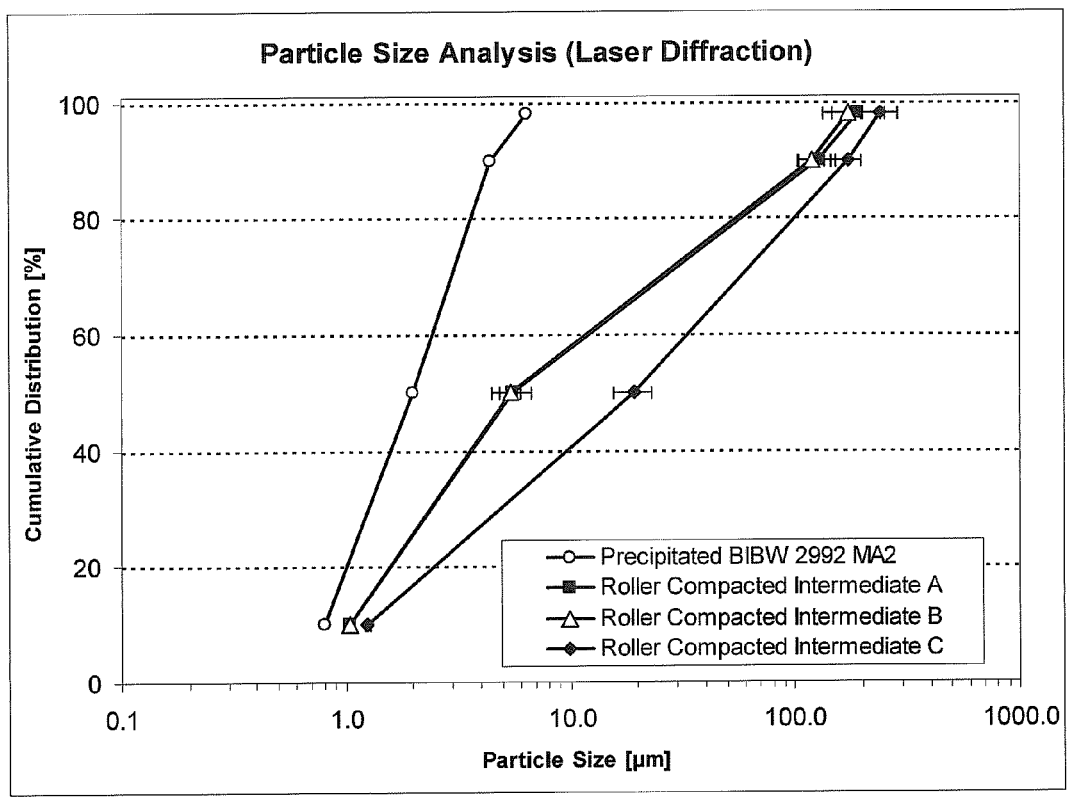
Roller Compaction Stages:   A→   C   =   Increasing   Compaction   Force

Figure 6: Dissolution comparison BIBW 2992 MA$_2$ film-coated tablets 20 mg, 30 mg, 40 mg, 50 mg in 0.1 M hydrochloric acid, pH 1.0; paddle 75 rpm / n=12
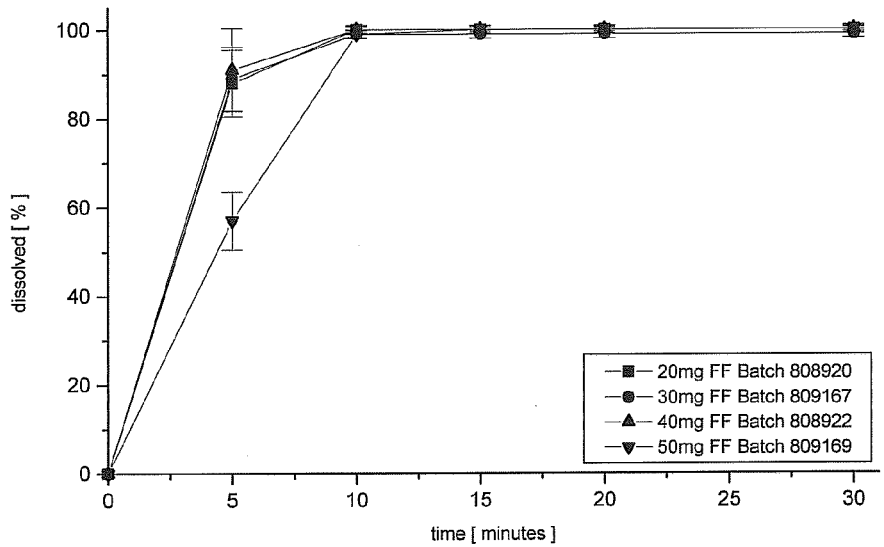
Figure 7: Dissolution comparison BIBW 2992 MA$_2$ film-coated tablets 20 mg, 30 mg, 40 mg, 50 mg in McIllvaine buffer, pH 4.0; paddle 75 rpm / n=12
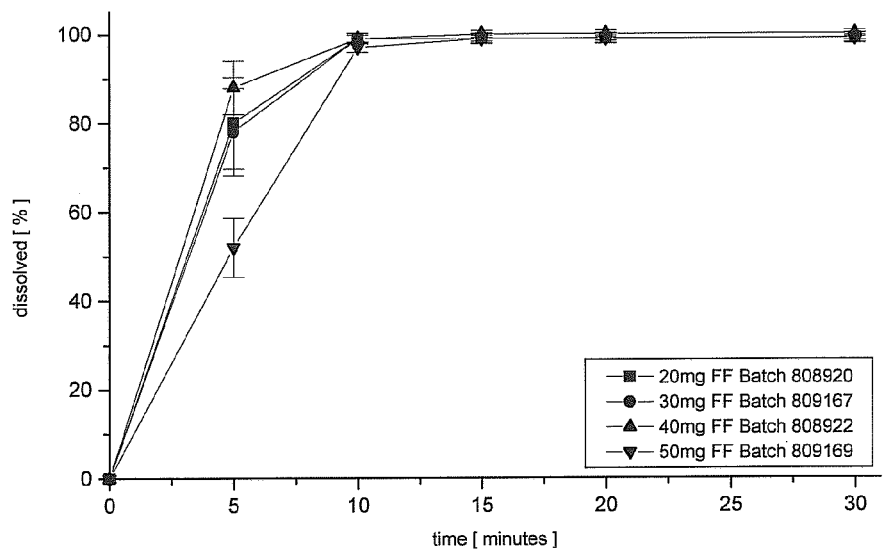

Figure 8: Dissolution comparison BIBW 2992 MA$_2$ film-coated tablets 20 mg, 30 mg, 40 mg, 50 mg in 0.05 M phosphate buffer, pH 6.8; paddle 75 rpm / n=12
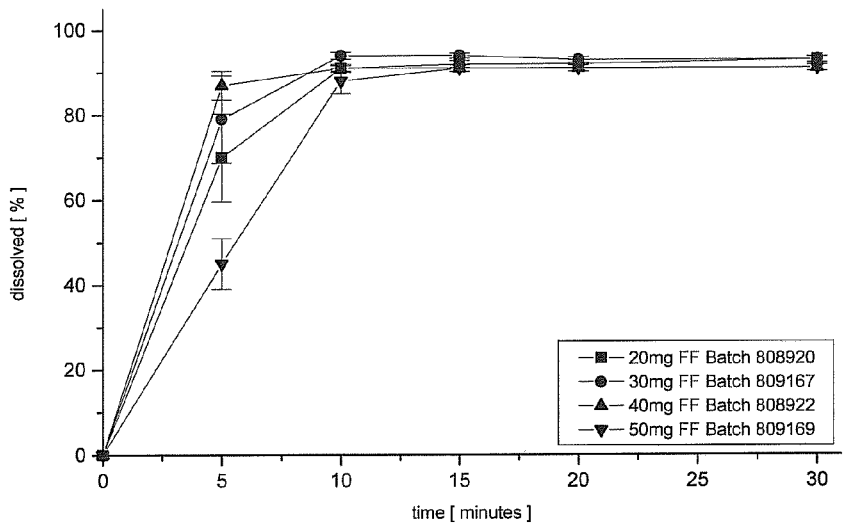
Figure 9: Dissolution comparison BIBW 2992 MA$_2$ film-coated tablets 20 mg, 30 mg, 40 mg, 50 mg in water; paddle 50 rpm / n=12
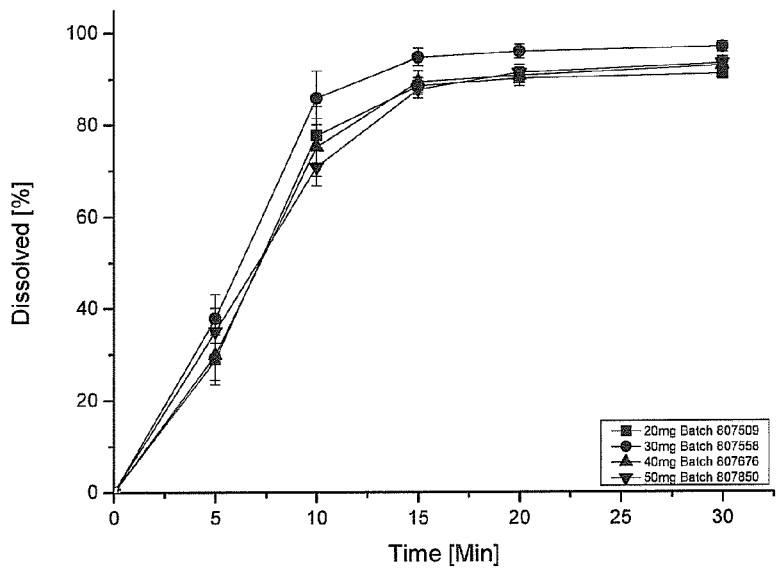

Figure 10:   Individual and geometric mean drug plasma concentration-time profiles of BIBW 2992 BS after multiple oral administration of 40 mg q.d. BIBW 2992 MA₂ tablets for 27 days in TP 1 (N=17)
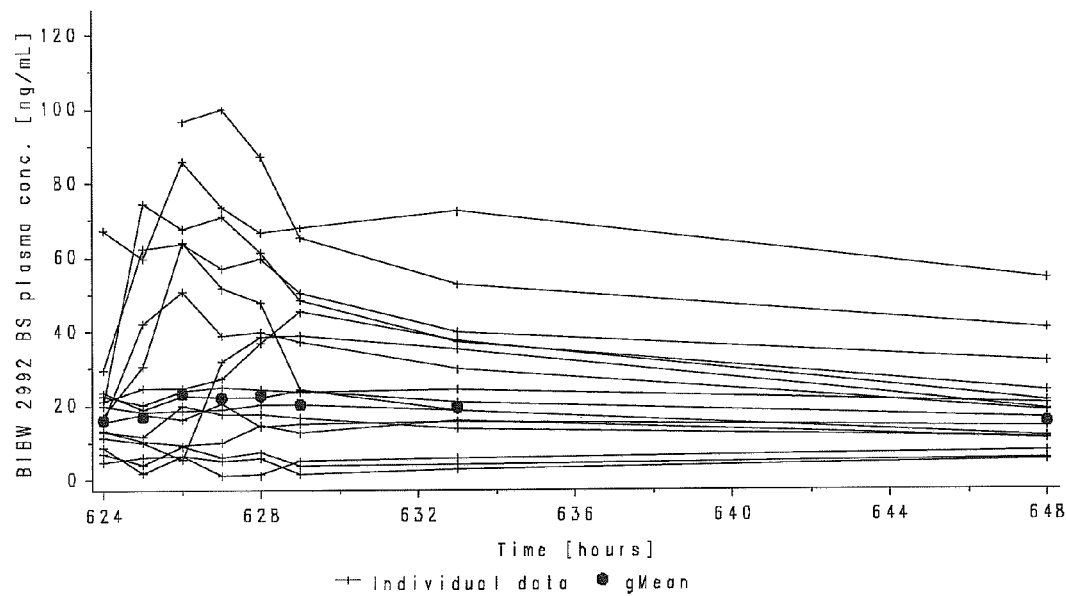
Figure 11:   Individual and geometric mean dose normalized maximum plasma concentrations of BIBW 2992 at steady state from four Phase I trials
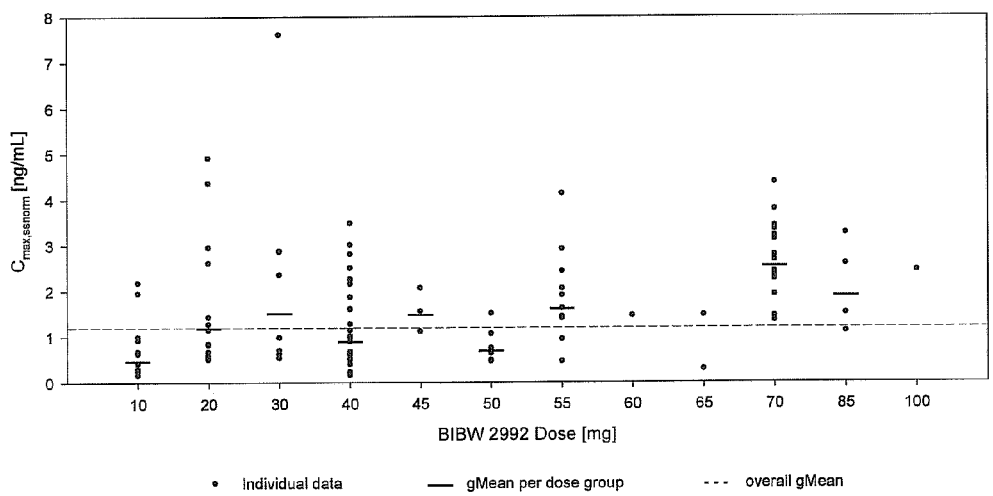

Figure 12: Individual and geometric mean dose normalized AUCτ,ss values of BIBW 2992 at steady state from four Phase I trials
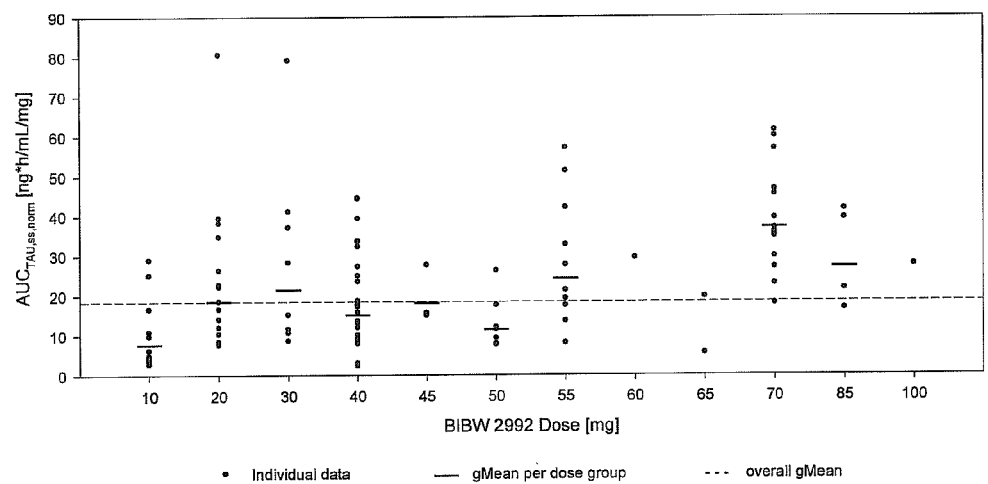
Figure 13: Individual and geometric mean dose normalized maximum plasma concentrations at Day 1 of Treatment Period 1 from one Phase I trial
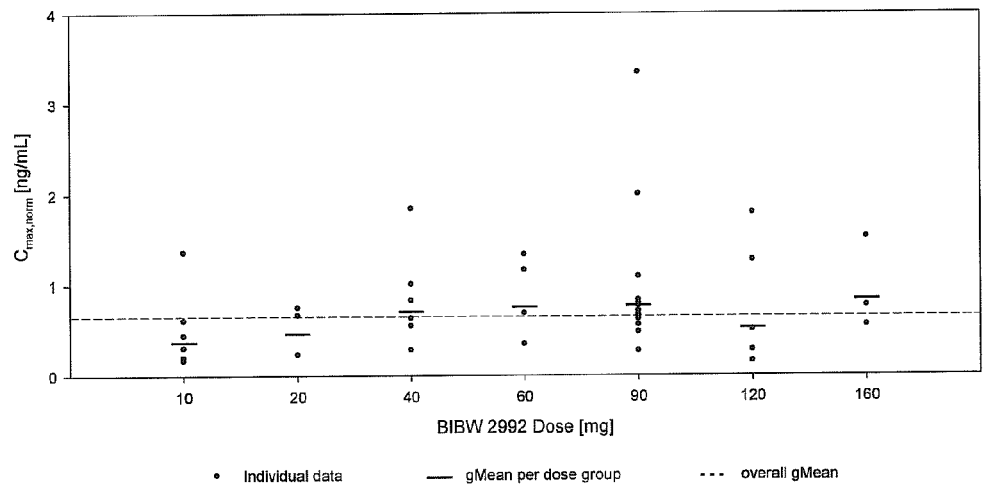

Figure 14: Individual and geometric mean dose normalized AUC$_{0-24}$ values of BIBW 2992 at Day 1 of Treatment Period 1 from one Phase I trial
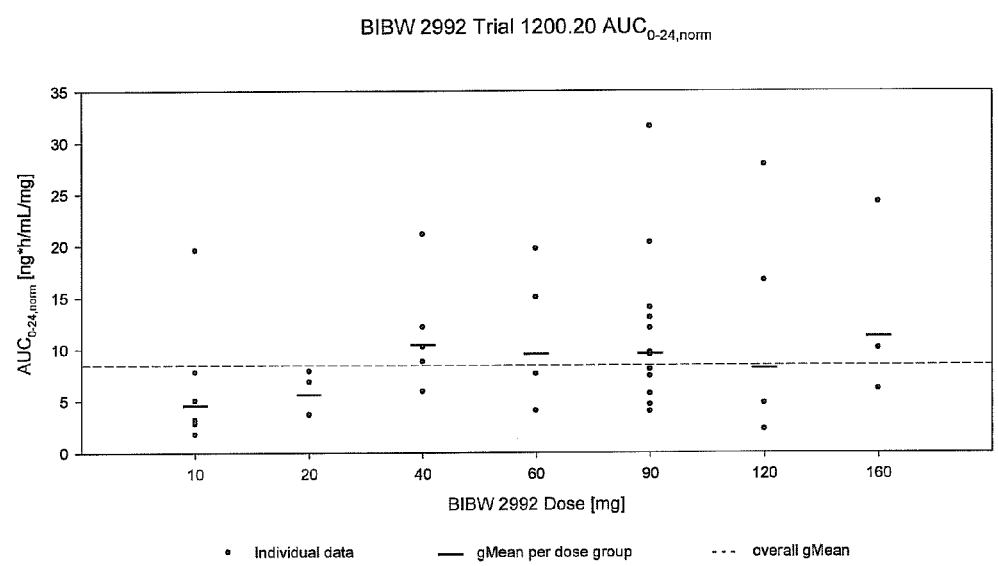

SOLID PHARMACEUTICAL FORMULATIONS COMPRISING BIBW 2992

FIELD OF THE INVENTION

The present invention relates in one aspect to a pharmaceutical dosage form containing the active substance BIBW 2992 as the dimaleate salt, providing an immediate release dissolution profile of the drug product.

According to a second aspect the present invention relates to compacted intermediates comprising the precipitated dimaleate salt of BIBW 2992, abbreviated hereinafter BIBW 2992 $MA_2$, in form of a powder obtainable by a combined compaction (either roller compaction, briquetting or slugging) and subsequent one or multiple sieving steps from BIBW 2992 $MA_2$, optionally in mixture with a lubricant such as magnesium stearate, intermediate blends prepared from said compacted intermediate, as well as solid oral formulations providing an immediate release dissolution profile, made from said compacted intermediate or from said intermediate blends ready for use/ingestion, e.g. as oral powders or capsule and tablet formulations such as uncoated or film-coated tablets prepared by direct-compression. The present invention also provides methods for producing the compacted intermediates, intermediate blends and solid oral formulations mentioned hereinbefore.

BACKGROUND OF THE INVENTION

The rate and extent to which the active ingredient is absorbed from a pharmaceutical dosage form and becomes available at the site of action is defined as bioavailability (Chen, M. L. et al., Bioavailability and bioequivalence: an FDA regulatory overview, Pharm. Res. 2001, 18, 1645-1648). However, it is rarely feasible to measure the drug at the site of action. Therefore, bioavailability is assessed based on drug concentrations in the general circulation. The systemic exposure is determined by measuring the blood or plasma concentrations of the active drug at numerous time points following the drug administration and calculation of the area under the concentration-time curve (AUC). Blood/plasma drug concentration time profiles are affected by the dynamics of dissolution, solubility, absorption, metabolism, distribution, and elimination.

In principal drug absorption from a solid oral dosage form after administration can depend on the dissolution of the solid oral dosage form, which results from a series of simultaneous and successive processes and the permeability across the gut wall of the gastrointestinal tract. Depending on the Biopharmaceutical Classification System (BCS) of the drug substance in vitro dissolution may be relevant to the prediction of in vivo plasma concentrations and therefore bioavailability (Guidance for Industry, Dissolution Testing of Immediate Release Solid Oral Dosage Forms, U.S. Department of Health and Human Services, Food and Drug Administration, Center for Drug Evaluation and Research (CDER), August 1997).

Based on this general consideration, in vitro dissolution tests for immediate release solid oral dosage forms, such as tablets and capsules, are used to assess the quality of a drug product. An immediate release product allows the ingredient or active moiety to dissolve in the gastrointestinal tract, without causing any delay or prolongation of the dissolution or absorption of the drug. Requirements for dissolution testing of immediate release products are focused in the Guidance for Industry (CDER 1997) "Dissolution testing for immediate release solid oral dosage forms", (CDER 1997) "Immediate release solid oral dosage forms—Scale up and Postapproval Changes", ICH Guidance Q6A, Specifications: Test Procedures and Acceptance Criteria For New Drug Substances And New Drug Products. The most commonly employed dissolution test methods as described in the European Pharmacopeia 6.3 ($6^{th}$ edition) are the basket method (Apparatus 1) and the paddle method (Apparatus 2). The described methods are simple, robust, well standardized, and used worldwide. They are flexible enough to allow dissolution testing for a variety of drug products. The following parameters influencing the dissolution behaviour may for example be relevant for selecting the appropriate in vitro dissolution test conditions for an immediate release solid oral product: Apparatus, stirring speed, dissolution medium and temperature.

BIBW 2992 is known as the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline,

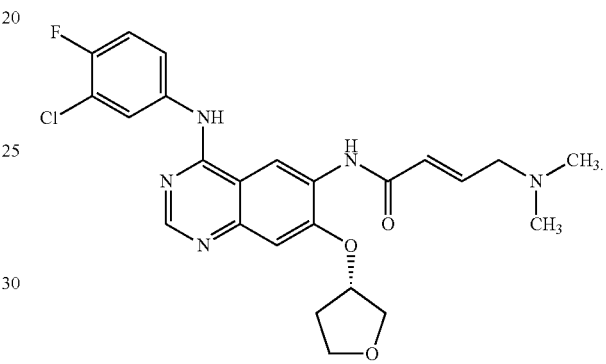

BIBW 2992 is a potent and selective dual inhibitor of erbb1 receptor (EGFR) and erbB2 (Her2/neu) receptor tyrosine kinases. Furthermore, BMW 2992 was designed to covalently bind to EGFR and HER2 thereby irreversibly inactivating the receptor molecule it has bound to. This compound, salts thereof such as the dimaleate BIBW 2992 $MA_2$ and its crystalline modification, their preparation as well as pharmaceutical formulations comprising BIBW 2992 or a salt thereof are disclosed in WO 02/50043 and WO 2005/037824. These documents are incorporated by reference regarding these aspects. BIBW 2992 BS mentioned hereinafter means the compound as the free base, identical with BIBW 2992 as characterized by the formula above.

BIBW 2992 is suitable for the treatment of tumoral diseases, hypersecretory diseases of the lungs and respiratory tract, diseases of the gastrointestinal tract, the bile duct and gall bladder. Indications to be treated with BIBW 2992 and combination treatments are disclosed in WO 2007/054550 and WO 2007/054551.

General Aspects of the Problem Underlying the Invention

Besides the pharmacological activity of an active pharmaceutical ingredient (API) there are a variety of physical or physicochemical characteristics of the active substance relevant for the preparation of solid oral dosage forms, as oral powders, granules, pellets, tablets, capsules, chewable tablets, dispersible tables, troches or lozenges. To achieve adequate formulation characteristics, as correct assay, content and mass uniformity, chemical and physical stability of the drug product and a proper dissolution rate, also the characteristics of the product intermediates have to be adequate for robust, fast and cost efficient processing.

Without being restrictive, examples of these parameters relevant for processing of the active agent (the drug substance) are
the stability of the drug substance under various environmental conditions which strongly may influence the stability of the final phaimaceutical formulation (the drug product), and physical characteristics of the drug substance such as bulk densities (i.e. poured and tapped density) or deriving hausner factor (Table 1), particle morphology, shape, the ratio of length to width for needles, size distribution, electrostatic charging and surface adhesive properties, which may vary due to precipitation and drying conditions of the drug substance. These characteristics may significantly influence key features for processing of the drug substance into a final formulation, such as flowability and compressibility.

TABLE 1

Hausner Factor and corresponding Flow Properties

| Hausner Factor | Flow Properties |
| --- | --- |
| 1.05-1.18 | Excellent |
| 1.14-1.19 | Good |
| 1.22-1.27 | Acceptable |
| 1.30-1.54 | Bad |
| 1.49-1.61 | Very bad |
| >1.67 | No flow |

The Hausner factor is the ratio of bulk volume to compacted volume, calculated by the formula bulk density/tapped density. Bulk density is measured according to Ph. Eur. 2.9.15 (European Pharmacopoeia, 4. Ed.) as poured density. The tapped density is measured according to Ph. Eur. 2.9.15 (see also Voigt R., Lehrbuch der pharmazeutischen Technologie [Textbook of Pharmaceutical Technology], Verlag Chemie, 5th Edition, page 148). The Hausner factor is a measure for the flowability/compressibility of powders and ideally should be close to 1.

These characteristics are important to impede segregation of the API inside the powder mixture during its movement e.g. in pipes, hopper and feeder of the tablet press. They ensure a reproducible and uniform API content within one drug product batch, particularly in low dose formulations or direct compression processes. Furthermore, these characteristics greatly influence parameters such as the flowability, compressibility, cohesiveness and lubrication of the drug substance or of mixtures thereof with excipients and thus may be critical to processability in automated production.

For production of tablets free flow of material into the die is necessary to ensure adequate and reproducible tablet mass and tablet hardness. The material must also possess some degree of cohesiveness to keep the compact from crumbling and falling apart on handling. Lastly, the material should have a degree of lubrication in order to minimize friction between material, punches and dies during tableting and to allow for the removal of the tablet. With regard to compactions to be used as final dosage forms, they must also possess a suitable degree of hardness, disintegration ability and speed and uniformity.

Finally, the properties of the pharmaceutical composition as such decisively contribute to the bioavailability of the active agent and hence efficacy of the medicament in the intended medical use.

In order to improve such properties of the drug substance which are relevant to manufacture the active compound into a solid oral pharmaceutical formulation meeting the criteria/standards defined by the regulatory authorities and the specific needs given by the therapeutic target profile (such as a defined bioavailability and pharmacokinetic profile) several physical or physicochemical processes may be applied, e.g. recrystallization, transformation into different polymorphic forms, mixture with several excipients or auxiliary material, comminution in order to reduce the particle size to a suitable level, or transformation of the drug substance into intermediate solid forms which may be further processed, such as conversion of powders to granules.

Comminution in its broadest sense is the mechanical process of reducing the size of particles or aggregates and embraces a wide variety of operations including cutting, chopping, grinding, crushing, milling, micronizing and trituration. Materials are often comminuted to improve compressibility. Compressibility of materials is influenced significantly by particle size or surface area of the particle.

Since degradation and/or amorphization of the pharmaceutically active substance as a side effect of the grinding (or micronising) has to be avoided as far as possible, in spite of the hard conditions required during the process, it is absolutely essential that the active substance should be highly stable throughout the grinding process. Only if this is fulfilled it is possible to produce a homogeneous pharmaceutical formulation which always contains the specified amount of active substance in reproducible manner.

Also the process of comminution is influenced by material properties as shape or melting point. Materials inadequate in these aspects might block the grinding chamber during the process uneconomically interrupting it which makes cleaning operations necessary.

Conversion of powders to granules (a small cohesive mass made up of a plurality of powder particles) may be a further approach covering inadequate physico-chemical API characteristics frequently offering a number of advantages including improving uniformity of the blend, improving uniformity of particle size, reducing dust hazards, allowing improved product flow, improving uniform bulk density, controlling particle hardness and improving dispersability. The most commonly employed granulation methods are wet-granulation, dry-granulation and hot-melt granulation.

In wet-granulation, a liquid binder solution is combined with a bed of mixed powders to mass the particles together into granules. The damp mass is then screened, dried and milled to the desired size.

The mass may also be dry screened, lubricated and compressed or extruded through a perforated screen and then dried. In drying, it is often desirable to maintain a residual amount of moisture in the granulation in order to maintain a hydrated state and to reduce static electric charges on the particles. Moisture content of the granulation should be uniform. Wet granulation suffers from a number of disadvantages. A chief disadvantage is the number of separate steps involved, as well as the time and labor necessary to carry out the procedure. Further, the use of aqueous solvents is limited by the stability of the product to be granulated. Explosion concerns and environmental regulations may limit the use of certain organic solvents.

Dry granulation may be used if the materials have sufficient inherent binding or cohesive properties to form granules. Dry granulation refers to the process of granulating without the use of liquids. In order for a material to be dry granulated at least one of its constituents, either the active ingredient or a diluent, must have cohesive properties. Dry granulation may be performed by a process known as "slugging." In "slugging" the material to be granulized is first made into a large compressed mass or "slug" typically by way of a tablet press using large flat-faced tooling (an example of a linear press is illustrated in U.S. Pat. No. 4,880,373). A fairly dense slug may be formed by allowing sufficient time for the air to escape from the material to be compacted. Compressed slugs are then comminuted through a desired mesh screen manually or automatically as, for example, by way of a comminuting mill. Formation of granules by "slugging" is also known as precompression. When tablets are made from the granulated slugged material, the process is referred to as the "double compression method."

Dry granulation may also be performed using a "roller compactor." In a roller compactor material particles are consolidated and densified by passing the material between two high-pressure rollers. The densified material from a roller compactor is then reduced to a uniform granule size by milling. The uniform granules may then be mixed with other substances, such as a lubricant, to tablet the material (as, for example, by way of a rotary tableting machine). In addition to pharmaceutical use, roller compaction is used in other industries, such as the food industry, animal feed industry and fertilizer industry.

Dry granulation of the API with excipients, predominantly binders like sugars, inorganic materials, as calcium hydrogen phosphate, cellulose or its derivates, may be an efficient and useful method of granulation. Especially when the API is susceptible for moisture and stability of the final product may be affected by wet-granulation techniques.

But it also bears challenges, as compressibility of the obtained granules decreases for a second compaction step to tablets. As a result by compressing dry granulated powders into tablets, lower tablet hardness and retarded disintegration is achieved, mainly by reduction of the porosity of the system. If porosity is too low, no water can be channeled into the tablet core supporting disintegration. Therefore often only parts of the employed excipients are added in the dry granulation step to ensure adequate hardness and disintegration speed of the tablet.

Roller compaction as most common dry granulation process is capable of handling a large amount of material in a short period of time. As a special subtype briquetting utilizes special designed compaction rolls which divides the compacted powder in pieces (briquetts). Dry granulation by "slugging" may be slow, inefficient, and many times requires several attempts at a successful formulation to ensure material flow. For dry granulation the compaction force in extend and uniformity of distribution is essential in regard to uniformity of granules' porosity to ensure uniform hardness and disintegration of the final product.

Melt granulation is a process by which powders are agglomerated with the aid of a binder, in either a molten state or a solid state that melts during the process. The apparatus of choice is a high-shear mixer, where the temperature of a powder can be raised above the melting point of a meltable binder by either a heating jacket or frictional forces generated by the impeller blades. Determination of the granulation endpoint regarding temperature is crucial for the melt granulation. Therefore the process is difficult to control. Furthermore, often the granulation mass adheres to the walls of the granulator bowl generating a not uniform mass regarding distribution of the components, content uniformity of the API and particle size distribution.

EP 0 241 126 A1 discloses a pharmaceutical composition comprising granules consisting of an aggregate of crystals of ibuprofen, providing better flow properties than bulk crystalline ibuprofen. The composition is produced by compaction of crystalline ibuprofen to form a granular aggregate containing no excipients. The processes used for compaction include compaction between rollers, extrusion or compaction in a granulation bowl.

EP 0 172 014 A1 discloses a pharmaceutical composition in granular form suitable for further processing comprising 85 to 99% by weight of ibuprofen, 15-1% by weight of croscarmellose sodium and, optionally, 0.4 to 1% by weight of colloidal silicon dioxide as excipients, prepared by passing the mixture through a roller compactor or a slugging operation and screening the compacted or slugged composition through a vibratory sieve or series of screens.

Specific Aspects of the Problem Underlying the Invention

BIBW 2992 $MA_2$ as described in WO 2005/037824 shows the following challenging physico-chemical properties relevant for processability in the preparation of a solid oral dosage form:

susceptibility against moisture affecting the chemical stability of the API and leading to decrease of the active principle and increase of contamination with hydrolytic degradation products;

needle shape of the precipitated active ingredient, causing a high variation of its low poured density due to random arrangement and length of the needles, poor flow properties due to increased resistance of the needles to align in flow direction, capping or laminating of tablets during a direct compression process due to entrapment of too much air inside the final blend, low compressibility, also in combination with additional excipients such as binders or fillers leading to mechanically weak granules in a dry-granulation process with subsequent segregation tendencies of the API during tableting due to crumbeling of these granules, and adhesive properties of the API on surfaces due to increased electrostatic charging leading to a selective reduction of BIBW 2992 $MA_2$ in a powder mixture during processing and therefore lack of API in the produced tablets, which would show in a inadequate assay value.

Precipitated BIBW 2992 $MA_2$ exhibits a random variability of its poured densities. They range from 0.12 to 0.40 g/mL, caused by different needle lengths (Table 2).

TABLE 2

Batch-to-batch variability of bulk densities of un-milled BIBW 2992 MA2

| Batch # | Poured density $(\rho_P)$ [g/mL] | Tapped density $(\rho_T)$ [g/mL] | Hausner Factor $(\rho_T/\rho_P)$ |
|---|---|---|---|
| 0 | 0.23 | 0.28 | 1.20 |
| 1 | 0.12 | 0.16 | 1.33 |
| 2 | 0.40 | 0.43 | 1.08 |
| 3 | 0.31 | 0.39 | 1.26 |

The variation of more than 100% is unacceptable for a robust manufacturing process. Especially in formulations containing amounts of API greater than 10% the effect on a direct compression is predominant by the lack of dilution which would equilibrate or cover the unfavourable physico-chemical properties of BIBW 2992 $MA_2$ as explained in the following:

BIBW 2992 MA$_2$ powder as obtained has poor flowability when used in a direct tableting process. This requires a substantial reduction of the standard tableting speed and causes high variation of compaction force and tablet mass due to incomplete filling of the dies. Since the powder is very voluminous the target tablet mass and acceptable tablet hardness can not be achieved. Furthermore, high compaction forces applied in the tableting process leads to capping whereas low compaction forces lead to sticking of the tablets.

The aim of the subject invention therefore is to provide BIBW 2992 MA$_2$ in a solid powdery form suitable for further processing into solid pharmaceutical formulations for oral administration in commercial scale which meets the stringent requirements imposed on pharmaceutical compositions. This has to be achieved regardless to the initial bulk densities as discussed above.

Several approaches to improve the properties of BIBW 2992 MA$_2$ drug substance relevant for processability in production scale, that is to transform the drug substance into a suitable form for the manufacture of a solid oral pharmaceutical composition failed, e.g. re-crystallization experiments did not yield BIBW 2992 MA$_2$ meeting the required properties.

For precipitated actives with the displayed physico-chemical properties usually various granulation techniques are applied. Wet granulation was not suitable, as the API underwent hydrolytical decomposition and further degradation reaction during processing.

Experiments with precipitated API using dry granulation processing yielded a product varying in poured density with poor physical stability of the granules. As a result the API did not form a persistent union with the other excipients and separated during the further processing. Hence the needles of BIBW 2992 MA$_2$ ascended during movement in the mixture leading to a not uniform blend. Therefore the content of the first tablets produced was to low while the tablets in the end contained an excess of API. In total the uniformity of the API content uniformity in the batch was inadequate. Furthermore, disintegration and hardness of the tablets obtained from the dry-granulated API was dissatisfactory due to the twofold compaction of the mixture.

Whereas experiments with milled API applying dry granulation yielded stable granules with excellent content unity and a product not containing needle-shaped crystals in the final blend, disintegration of the tablets obtained was unsatisfactorily prolonged due to increased surface area of the soluble API.

Further drawbacks were a high amount of fines in the granules leading to variation of the compression force.

Hot melt granulation with precipitated API also yielded stable granules with excellent content uniformity and a product not containing needle-shaped crystals in the final blend, nevertheless, drawbacks of this approach were variation of the compression force needed to tablet the granules, a variation of poured density of the product and a tendency to form wall-adhesions inside the granulation bowl of the mixer.

The results summarized hereinbefore show that, practically, it is not possible to ensure a robust process and constant drug product quality for the varying physico-chemical characteristics of BIBW 2992 MA$_2$, simply applying standard state-of-the-art techniques by routine.

BRIEF SUMMARY OF THE INVENTION

According to a first aspect the aim of the present invention is to obtain a pharmaceutical dosage form for the above drug substance which meets adequate bioavailability requirements for the desired target dosage range and which is further characterized by a specific immediate release profile range providing an appropriate plasma concentration-time profile of the active principle. Such specific release profile characteristic is not known from the prior art for this drug substance.

A first object of the present invention is a pharmaceutical dosage form of the active substance BIBW 2992 MA$_2$ which provides an immediate release dissolution profile over the entire physiologically relevant pH range from pH 1-6.8 and water (900 mL dissolution medium, 50/75 rpm agitation speed and a temperature of 37° C.). The dissolution characteristics comply to recommended acceptance criteria for immediate release solid oral dosage forms of not less than 85% (Q=80%) dissolved in 60 minutes or less (Guidance for Industry, Dissolution Testing of Immediate Release Solid Oral Dosage Forms, U.S. Department of Health and Human Services, Food and Drug Administration, Center for Drug Evaluation and Research (CDER), August 1997). Preferably, not less than 85% (Q=80%) of the active substance BIBW 2992 MA$_2$ (API salt), is dissolved in 30 minutes or less, more preferred within 15 minutes.

A further object of the present invention is the above pharmaceutical dosage form which, under the above conditions, exhibits comparable in vitro dissolution profiles independent from a dosage strength of 1 to 160 mg of the active substance, preferably within a dosage strength range of 5 to 100 mg, or, more preferred, within a dosage strength range of 5 to 50 mg.

A further object of the present invention is a pharmaceutical dosage form of the active substance BIBW 2992 MA$_2$ which provides an immediate release profile in which the maximum concentration of the analyte/active substance in plasma at steady state ($C_{max,ss}$) increases in a dose-proportional manner, preferably when the dose range of the active substance is between 10 and 160 mg, preferably between 10 and 100 mg.

Any ranges provided in connection with the present invention are meant to include the limiting values, e.g. a range defined as "between 10 and 160 mg" includes the lower and upper limiting value of 10 and 160 mg.

A further object of the present invention is a pharmaceutical dosage form of the active substance BIBW 2992 MA$_2$ which provides an immediate release profile in which the dose-normalized maximum concentration of the analyte/active substance in plasma at steady state ($C_{max,ss,norm}$) is similar for different doses, preferably when the dose range of the active substance is between 10 and 160 mg, preferably between 10 and 100 mg.

A further object of the present invention is a pharmaceutical dosage form of the active substance BIBW 2992 MA$_2$ which provides an immediate release profile in which the area under the plasma concentration-time curve of the analyte/active substance in plasma at steady state over a dosing interval $\tau$ ($AUC_{\tau,ss}$) increases in a dose-proportional manner, preferably when the dose range of the active substance is between 10 and 160 mg, preferably between 10 and 100 mg.

A further object of the present invention is a pharmaceutical dosage form of the active substance BIBW 2992 MA$_2$ which provides an immediate release profile in which the dose-normalized area under the plasma concentration-time curve of the analyte/active substance in plasma at steady state over a dosing interval $\tau$ ($AUC_{\tau,ss,norm}$) is similar for different doses, preferably when the dose range of the active substance is between 10 and 160 mg, preferably between 10 and 100 mg.

A further object of the present invention is a pharmaceutical dosage form of the active substance BIBW 2992 MA$_2$ which provides an immediate release profile, characterized in that it reaches a maximum plasma concentration in the plasma of cancer patients between 0.75 and 7 hours, preferably with a median value between 1 to 6 hours after single dose as well as at steady state.

A further object of the present invention is a pharmaceutical dosage form of the active substance BIBW 2992 $MA_2$ which provides an immediate release profile, wherein the maximum plasma concentration at steady state in the plasma of cancer patients with various advanced solid tumors is at least within a range of 5 ng/ml and 100 ng/ml, with a geometric mean value between 15 to 35 ng/ml, if a dosage form comprising 20 mg of BIBW 2992 $MA_2$ (API salt) has been administered once daily for a period of at minimum 14 days.

A further object of the present invention is a pharmaceutical dosage form of the active substance BIBW 2992 $MA_2$ which provides an immediate release profile, wherein the maximum plasma concentration at steady state in the plasma of cancer patients with various advanced solid tumors is at least within a range of 5 ng/ml and 30 ng/ml, with a geometric mean value between 25 to 120 ng/ml, if a dosage form comprising 30 mg of BIBW 2992 $MA_2$ (API salt) has been administered once daily for a period of at minimum 14 days.

A further object of the present invention is a pharmaceutical dosage form of the active substance BIBW 2992 $MA_2$ which provides an immediate release profile, wherein the maximum plasma concentration at steady state in the plasma of cancer patients with various advanced solid tumors is at least within a range of 5 ng/ml and 230 ng/ml, with a geometric mean value between 25 to 120 ng/ml, if a dosage form comprising 40 mg of BIBW 2992 $MA_2$ (API salt) has been administered once daily for a period of at minimum 14 days.

A further object of the present invention is a pharmaceutical dosage form of the active substance BIBW 2992 $MA_2$ which provides an immediate release profile, wherein the maximum plasma concentration at steady state in the plasma of cancer patients with various advanced solid tumors is at least within a range of 5 ng/ml and 230 ng/ml, with a geometric mean value between 35 to 120 ng/ml, if a dosage form comprising 50 mg of BIBW 2992 $MA_2$ (API salt) has been administered once daily for a period of at minimum 14 days.

A further object of the present invention is the above pharmaceutical dosage form, wherein it is an orally deliverable dosage form.

A further object of the present invention is the above pharmaceutical dosage form which is in the form of a tablet, capsule, pellets, powder or granules.

A further object of the present invention is the above pharmaceutical dosage form for use as medicament.

A further object of the present invention is the above pharmaceutical dosage form for use as pharmaceutical composition with an antiproliferative activity.

A further object of the present invention is the above pharmaceutical dosage form for the treatment of a disease or condition selected from oncological diseases.

A further object of the present invention is the use of the above pharmaceutical dosage form for the preparation of a medicament for the treatment of a disease or condition selected from oncological diseases.

A further object of the present invention is a process for the treatment and/or prevention of a disease or condition selected from oncological diseases, characterised in that an effective amount of the above defined pharmaceutical dosage form is administered orally to a patient once or several times daily.

According to a second aspect the present invention is directed to a compacted intermediate comprising BMW 2992 $MA_2$ in form of a powder obtainable by a combined compaction (either roller compaction, briquetting or slugging) and subsequent sieving of the compacted active, optionally in mixture with a lubricant, to adjust and equilibrate its bulk properties and therefore ensure its suitability for further processing into a finished dosage form.

A further object of the present invention is directed to intermediate and final blends prepared from said compacted intermediate, suitable for further processing in the preparation of solid oral dosage forms.

A further object of the present invention is directed to solid oral formulations made from said compacted intermediate or from said intermediate blends or from said final blends, ready for use/ingestion, e.g. capsule and tablet formulations such as uncoated or film-coated tablets prepared by direct-compression A further object of the present invention is directed to methods for producing the compacted intermediates, intermediate blends and solid oral formulations mentioned hereinbefore.

DETAILED DESCRIPTION OF THE INVENTION

Dissolution Characteristics and Pharmacokinetic Properties

The dissolution tests for performing the in vitro comparison of four dosage strengths (20, 30, 40, 50 mg) of BIBW 2992 $MA_2$ film-coated tablets described in the Examples (Table 4) use Apparatus 2 (paddle) according to European Pharmacopeia 6.2, and are described in the following:

| | |
|---|---|
| Instrument: | Apparatus 2 (paddle) |
| Paddle speed: | 50/75 rpm |
| Dissolution medium: | 0.05M phosphate buffer pH 6.8 |
| | Mc Ilvaine buffer pH 4.0 |
| | 0.1M HCl pH 1 |
| | water (50 rpm) |
| Volume: | 900 ml |
| Sampling time points: | 5, 10, 15, 20, 30 min |
| Number of tablets (n): | 12 per dose strength |

Concentration measurement in the dissolution vessels was performed with HPLC-UV.

The dissolution profiles obtained with the 20, 30, 40, and 50 mg dosage strengths of BIBW 2992 $MA_2$ film-coated tablets according to the invention at pH 1.0, 4.0, 6.8, and water respectively, are shown in FIGS. 6-9. The mean values obtained for a sample of 12 film-coated tablets per batch and the y-error bars represent the calculated 95% confidence intervals. As can be seen from FIGS. 6-8 all four dosage strengths dissolved more than 85% after 15 minutes. Therefore, all four dosage strengths of the formulation are deemed equivalent. Based on the similar rapid in vitro dissolution behaviour of the four dosage strengths (20, 30, 40, 50 mg) of BIBW 2992 $MA_2$ film-coated tablets equivalent in vivo performance is expected.

In four Phase I studies in cancer patients with various advanced solid tumors the pharmacokinetik (PK) characteristics of BIBW 2992 were analyzed. Representative for all of the studies and all the tested dose groups (10 to 100 mg) the 40 mg dose group from one trial is being described in more detail. The individual and geometric mean (gMean) plasma concentration time profiles of BIBW 2992 after administration of 40 mg on day 27 (once daily administration) of Treatment Period 1 (first 28 days of treatment) are displayed in FIG. 10. BIBW 2992 plasma concentrations increased after oral administration with peak plasma concentrations mostly around 2-5 hours after dosing. Plasma concentrations declined within the next hours (up to 9 h after dosing), displaying a first disposition phase. A second disposition phase was observed in the time interval from 9 h to 24 h post dose. Based on these data, BIBW 2992 exhibited at least biexponential disposition kinetics.

FIG. 10 shows a high inter-individual variability of the plasma concentrations of the individual (n=17) patients of the 40 mg dose group. The variability (gCV=geometric coefficient of variation) of the plasma concentrations of the active substance at the different time points was 109-159% up to 9 hours after drug administration but 66.9 to 72.9% at later time points (24 hours after drug administration).

In four Phase I trials in cancer patients with various advanced solid tumors with BIBW 2992 monotherapy as well as in one trial of BIBW 2992 therapy together with docetaxel there was no sign for a deviation from a dose proportional increase in AUC and $C_{max}$ of the active substance observed through visual inspection neither after single dose nor at steady state for once daily dosing. As a consequence, in cancer patients gMean $C_{max,ss}$ and $AUC_{\tau,ss}$ of the active substance increased in a dose-proportional manner after single dose and at steady state, for qd (once daily) dosing. Representative for all $C_{max}$ as well as AUC values from the four phase I monotherapy trials the respective PK parameters at steady state are displayed in FIGS. 11 and 12. Representative for all $C_{max}$ as well as AUC values from the phase I combination trial of BIBW 2992 together with doecatxel the respective PK parameters of BIBW 2992 are displayed in FIGS. 13 and 14. There was no deviation from dose-proportionality observed for drug plasma concentrations measured before drug administration at steady state ($C_{pre,ss}$) in cancer patients in various clinical trials, found through visual inspection (data not shown).

Solid Formulations Comprising BIBW 2992 $MA_2$ and Methods for their Preparation It was found that the problem underlying the subject invention is solved by applying a compaction step (either roller compaction, briquetting or slugging) of the active ingredient BIBW 2992 $MA_2$ for densification of the material and one or multiple subsequent sieving steps for breaking-up of the ribbon as well as further particle size reduction and dispersion of the API prior to blending with all excipients and further direct compression.

Compacted Intermediate Comprising BIBW 2992 $MA_2$

One object of the present invention is directed to a compacted intermediate comprising BIBW 2992 $MA_2$ in form of a powder obtainable by a compaction step selected from roller compaction, briquetting or slugging, combined with at least one sieving step from BIBW 2992 $MA_2$ after compaction, optionally in mixture with a lubricant.

The compacted intermediate according to the invention in its broadest embodiment is BIBW 2992 MA, in form of a powder, comprising a lubricant in an amount of 0 to 2.0% calculated on the amount of API salt.

It is characterized by the following parameters:

Particle size distribution can be specified in the ranges according to Ph. Eur. 2.9.35 (European Pharmacopeia, 6.02 Ed.).

"x10" means a particle size corresponding to 10 percent of the cumulative undersize distribution.

"x50" means a median particle size, i.e. 50 percent of the particles are smaller and 50 percent of the particles are larger than x50.

"x90" means a particle size corresponding to 90 percent of the cumulative undersize distribution.

In the broadest embodiment the particle size distribution is characterized by the ranges x10<200 μm, 1 μm<x50<300 μm, 75 μm<x90<600 μm;

preferably by the ranges x10<100 μm, 1 μm<x50<200 μm, 75 μm<x90<400 μm;

and, most preferred and as exemplarily shown in FIG. 4 and FIG. 5, by the ranges:

x10<5 μm, 1 μm<x50<100 μm, 75 μm<x90<200 μm and x100<1000 μm.

Poured Density ($\rho_p$) can be specified in the ranges: 0.2 g/mL<$\rho_p$<1.0 g/mL Hausner Factor (HF) can be specified in the ranges: 1.00<HF<1.30.

Intermediate Blends Prepared from the Compacted Intermediate of BIBW 2992 $MA_2$ A further object of the present invention is directed to intermediate and final blends prepared from the compacted intermediate comprising BIBW 2992 $MA_2$, suitable for further processing in the preparation of solid oral dosage foi ins, as defined hereinbefore with regard to the compacted intermediate.

Intermediate and final blends according to the invention in their broadest embodiments are characterized by contents selected from components (a) to (g):

(a) compacted intermediate of BIBW 2992 according to the first object of the invention in an amount of about 1 to 99% by weight, (b) optionally one or more carriers in an amount of about 10 to 99% by weight, (c) one or more binders in an amount of about 0 to 99% by weight, preferably 1 to 99% by weight, (d) one or more glidants in an amount of about 0 to 10% by weight, preferably 0.1 to 10% by weight, (e) one or more disintegrants in an amount of about 0 to 10% by weight, preferably 0.1 to 10% by weight, (f) one or more lubricants in an amount of about 0 to 10% by weight, preferably 0.1 to 10% by weight, and (g) 0 to 10% by weight of further excipients and/or adjuvants, wherein presence of at least one of components (b) to (g) is mandatory but also two up to at most all six of the optional components (b) to (g) are allowed to be present in addition to component (a) in the intermediate and final blends, the sum of all components adding to 100%.

For the avoidance of doubt, the primary purpose of glidants is to improve flowability of a powder whereas lubricants prevent ingredients from clumping together, e.g. from sticking to the tablet punches or capsule filling machine. Lubricants also ensure that tablet formation can occur with low friction between the solid and die wall.

As a matter of course any of the auxiliary components (a) to (g) mentioned generically or specifically must be edible and pharmacological acceptable.

The carrier component (b) may be solid organic, as sugars, (e.g. monosaccharides like glucose; oligosaccharides like sucrose, or disaccharides, as lactose in various crystalline modifications, as precipitated, spray-dried, drum-dried, or co-processed with further excipients as microcrystalline cellulose, or sorbitol, mannitol, xylitol, lactitol, erythritol, dulcitol, ribitol, erythritol), cellulose and its derivates (e.g. powdered cellulose or microcristalline cellulose)

starch or modified starches (e.g. pre-gelatinized, or partially hydrolysed), or solid inorganic, as
  calcium phosphate, dibasic calcium phosphate, hydroxyl apatite, calcium sulphate, calcium carbonate,
or semisolid as
  lipids or paraffin.

The binders (c) may be selected from
  cellulose and/or its derivates as microcrystalline cellulose, ethylcellulose, carboxymethylcellulose, hydroxypropylmethylcellulose, hydroxyethylcellulose,
  starch or modified starches (e.g. pre-gelatinized, or partially hydrolysed),
  polyethyleneglycols
  polyvinylpyrrolidones (e.g. Kollidon® K30), polyvinylacetates, polyvinylalcohols or co-polymerisates thereof (e.g. Copovidone).

The glidants (d) may be selected from colloidal silica, light anhydrous silicic acid, crystalline cellulose, talc, or magnesium stearate.

The disintegrants (e) may be selected from sodium starch glycolate, crospovidone, croscarmellose, sodium carboxymethylcellulose and dried corn starch.

The lubricants (f) may be selected from stearic acid, magnesium stearate, sodium stearylfumarate, glycerol tribehenate or polyethylene glycol.

The further excipients and/or adjuvants may be selected from any other components not falling under the definitions of components (b) to (f) or not specifically mentioned for components (b) to (f). Only exemplary, coloring agents including dyes and pigments such as iron oxide red or yellow, and titanium dioxide would fall under this category.

Preferred embodiments (1) and (2) of the intermediate blends according to the invention are characterized as follows (amounts are provided in % by weight of total intermediate blend):

| (1) | (1.1) | Compacted intermediate of BIBW 2992 MA$_2$: | 5%-50% |
|---|---|---|---|
|  | (1.2) | Carrier/binder or combination thereof: | 55%-95% |
|  | (1.3) | Disintegrant: | 0.5%-3.0% |
|  | (1.4) | Glidant: | 0.1%-2.0% |
|  | (1.5) | Lubricant: | 0%-2.0% |
|  | (1.6) | Further excipients and/or adjuvants | 0 to 5%. |

Any binary, ternary, quaternary or quinary combination comprising (1.1) and 1, 2, 3 or 4 of (1.2), (1.3) (1.4), (1.5) and (1.6), wherein the amounts of the components provided have been corrected due to absent components, are understood to be further preferred embodiments of intermediate blends.

| (2) | (2.1) | Compacted intermediate of BIBW 2992 MA$_2$: | 15%-30% |
|---|---|---|---|
|  | (2.2) | Carrier/binder or combination thereof: | 75%-85% |
|  | (2.3) | Disintegrant: | 1.5%-2.5% |
|  | (2.4) | Glidant: | 0.1%-1.0% |
|  | (2.5) | Lubricant: | 0%-1.0% |
|  | (2.6) | Further excipients and/or adjuvants | 0 to 3%. |

Any binary, ternary, quaternary or quinary combination comprising (2.1) and 1, 2, 3 or 4 of (2.2), (2.3) (2.4), (2.5) and (2.6), wherein the amounts of the components provided have been corrected due to absent components, are understood to be further preferred embodiments of intermediate blends.

Preferred embodiments (3), (4) and (5) of the final blends according to the invention are characterized as follows (amounts are provided in % by weight of total final blend):

| (3) | (3.1) | Compacted intermediate of BIBW 2992 MA$_2$: | 5%-50% |
|---|---|---|---|
|  | (3.2) | Carrier/binder or combination thereof: | 55%-95% |
|  | (3.3) | Disintegrant: | 0.5%-3.0% |
|  | (3.4) | Glidant: | 0.1%-2.0% |
|  | (3.5) | Lubricant: | 0.5%-3.0% |
|  | (3.6) | Further excipients and/or adjuvants | 0 to 1%. |

Any binary, ternary, quaternary or quinary combination comprising (3.1) and 1, 2, 3 or 4 of (3.2), (3.3) (3.4), (3.5) and (3.6), wherein the amounts of the components provided have been corrected due to absent components, are understood to be further preferred embodiments of intermediate blends.

| (4) | (4.1) | Compacted intermediate of BIBW 2992 MA$_2$: | 25%-35% |
|---|---|---|---|
|  | (4.2) | Carrier or Combination thereof: | 75%-85% |
|  | (4.3) | Disintegrant: | 0.5%-3.0% |
|  | (4.4) | Glidant: | 0.1%-2.0% |
|  | (4.5) | Lubricant: | 0.5%-3.0% |
|  | (4.6) | Further excipients and/or adjuvants | 0 to 1%. |

Any binary, ternary, quaternary or quinary combination comprising (4.1) and 1, 2, 3 or 4 of (4.2), (4.3) (4.4), (4.5) and (4.6), wherein the amounts of the components provided have been corrected due to absent components, are understood to be further preferred embodiments of intermediate blends.

| (5) | (5.1) | Compacted intermediate of BIBW 2992 MA$_2$: | 10%-25% |
|---|---|---|---|
|  | (5.2) | Carrier or Combination thereof: | 75%-85% |
|  | (5.3) | Disintegrant: | 0.5%-3.0% |
|  | (5.4) | Glidant: | 0.1%-2.0% |
|  | (5.5) | Lubricant: | 0.5%-3.0% |
|  | (5.6) | Further excipients and/or adjuvants | 0 to 1%. |

Any binary, ternary, quaternary or quinary combination comprising (5.1) and 1, 2, 3 or 4 of (5.2), (5.3) (5.4), (5.5) and (5.6), wherein the amounts of the components provided have been corrected due to absent components, are understood to be further preferred embodiments of intermediate blends.

Solid Oral Formulation Ready for Use/Ingestion

Solid oral formulations ready for use/ingestion made from the compacted intermediate of BIBW 2992 MA$_2$ or from intermediate blends comprise powders, granules, pellets, tablets, capsules, chewable tablets, dispersible tables, troches and lozenges.

Capsule formulations according to the invention comprise the powdery compacted intermediate of BIBW 2992 MA$_2$, an intermediate blend comprising the powdery compacted intermediate, pellets or granules obtained by conventional wet-, dry or hot-melt granulation of a suitable intermediate blend, filled in conventional capsules, e.g. hard gelatin or HPMC capsules.

Tablet formulations according to the invention comprise such tablets obtained by direct compression of a suitable final blend or by tableting of pellets or granules obtained by conventional wet-, dry or hot-melt granulation of a suitable intermediate blend.

The tablet formulations according to the invention may be uncoated or coated, e.g. film-coated, using suitable coatings known not to negatively affect the dissolution properties of the final formulation. For instance the tablets can be provided with a seal coat for protection of the patients environment and clinical staff as well as for moisture protection purposes by dissolving a high molecular weight polymer as polyvinylpyrrolidone or hydroxypropyl-methylcellulose together with plasticizers, lubricants and optionally pigments and tensides in water or organic solvent as acetone and spraying this mixture on the tablet cores inside a coating equipment as a pan coater or a fluidized bed coater with wurster insert.

Additionally, agents such as beeswax, shellac, cellulose acetate phthalate, polyvinyl acetate phthalate, zein, film forming polymers such as hydroxypropyl cellulose, ethylcellulose and polymeric methacrylates can be applied to the tablets, provided that the coating has no substantial effect on the disintegration/dissolution of the dosage form and that the coated dosage form is not affected in its stability.

After the dosage form is filmcoated, a sugar coating may be applied onto the sealed pharmaceutical dosage form. The sugar coating may comprise sucrose, dextrose, sorbitol and the like or mixtures thereof. If desired, colorants or opacifiers may be added to the sugar solution.

The solid oral formulations according to the present invention preferably contain 1 to 150 mg, more preferably 5 to 100 mg, of the API, based on BIBW 2992 (the amounts given in this paragraph and for the total composition of tablet formulations hereinafter are recalculated from the amounts of BIBW 2992 $MA_2$ to refer to the content of the free base BIBW 2992). Presently preferred forms comprise 5, 10, 20, 30, 40, 50, 70 or 100 mg of BIBW 2992, respectively.

For instance, the total composition of tablet formulations according to the invention may vary within the following ranges, with the proviso that the proportional composition given above with respect to the intermediate blends is met:
1 to 150 mg of BIBW 2992,
50 to 500 mg of carrier, binder or combination thereof
0.1 to 5 mg of a glidant,
1 to 15 mg of a disintegrant,
1 to 15 mg of a lubricant,
preferably
20 to 70 mg of BIBW 2992,
120 to 500 mg of carrier, binder or combination thereof
0.5 to 5 mg of a glidant,
2.5 to 15 mg of a disintegrant,
2.5 to 15 mg of a lubricant, Solid formulations of the present invention tend to be low hygroscopic. They may be packaged using PVC-blisters, PVDC-blisters or a moisture-proof packaging material such as aluminium foil blister packs, alu/alu blister, transparent or opaque polymer blister with pouch, polypropylene tubes, glass bottles and HDPE bottles optionally containing a child-resistant feature or may be tamper evident. The primary packaging material may comprise a desiccant such as molecular sieve or silica gel to improve chemical stability of the API. Opaque packaging such as colored blister materials, tubes, brown glass bottles or the like can be used to prolong shelflife of the API by reduction of photodegradation.

Process for Preparing Compacted Intermediates, Intermediate Blends and Solid Oral Formulations Another object of the present invention is directed to methods for producing the compacted intermediate of BIBW 2992 $MA_2$, the intermediate blends and the solid oral formulations mentioned hereinbefore.

Process for Preparing Compacted Intermediates

The compacted intermediate comprising BIBW 2992 $MA_2$ in form of a powder is obtainable by a compaction step selected from roller compaction, briquetting or slugging, combined with at least one sieving step additional to the break-up of the ribbon or briquettes, (FIG. 1), optionally in mixture with a lubricant.

The roller compaction step was introduced for densification of the material (see Table 3), which may have a variability of the poured density between 0.10 and 0.4 mg/mL (see Table 1) and
a Hausner Factor between 1.05 and 1.61 (see Table 1).

TABLE 3

Powder and Tablet Characteristics of BIBW 2992 $MA_2$ before and after introduction of Roller Compaction and Sieving

| | Drug Substance Batch | | | | | |
|---|---|---|---|---|---|---|
| | 1 | 1 | 1 | 1 | 2 | 3 |
| Poured density [g/mL] | 0.12 | 0.12 | 0.12 | 0.12 | 0.31 | 0.40 |
| Roller Compaction | No | | | Yes | | |
| Sieving 1 | No | | | Sieve A | | |
| Sieving 2 | No | No | Sieve B | | Sieve C | |
| Poured density [g/mL] of Compacted Intermediate of BIBW 2992 $MA_2$ | — | 0.33 | 0.29 | 0.24 | 0.41 | 0.36 |
| Poured density [g/mL] of Final Blend | 0.40 | 0.56 | 0.53 | 0.53 | 0.60 | 0.60 |
| RSD- Tablet Content [%] (Low Dose) | —* | 7.7 | 3.6 | 1.4 | —** | —** |
| RSD- Tablet Content [%] (High Dose) | —* | 3.4 | 1.4 | 1.0 | 0.8 | 1.7 |

RSD: Relative Standard Deviation
*Tableting not possible due to improper filling of the dies, sticking, laminating of tablets
**Not produced The roller compaction may be carried out with
API BIBW 2992 $MA_2$ alone or, optionally, with
a pre-blend of the API with 0 to 1.0% of a lubricant in a freefall or tumble blender to prevent major sticking on the compaction rolls.
Addition of a lubricant can be avoided if an agitated pre-blend is used and kept under agitation when loading onto the roller compactor.
The API or pre-blend of the API is compacted on a conventional roller compactor
optionally with horizontally, vertically or 45° angle alignment of the compaction rolls,
which may be smooth or shaped on their surface.
The compaction force may vary
between 1 kN/cm and 20 kN/cm,
preferably between 2 kN/cm and 10 kN/cm,
at a compaction speed of the compaction rolls
between 1 rpm and 30 rpm,
preferably between 1 rpm and 10 rpm,
and a gap width between the compaction rolls
between 1 mm and 10 mm
preferably between 1 and 5 mm.
The disintegration speed (FIG. 2) as well as dissolution speed (FIG. 3) of tablets prepared from the compacted intermediate can be increased by augmentation of the compaction force of the roller-compactor within the described limits.

The compacted intermediate is received from the compaction rolls in form of ribbons which are directly broken up into granules by a granulation-unit with a mesh size between 0.5 mm and 1.6 mm. Thus the compaction step according to the invention results the compacted intermediate in form of granules.

In the second step subsequently the granules are sieved by a sieving machine, as e.g. an oscillating or conical sieving machine or hammer mill, with a mesh size of 0.5 to 2.0 mm, preferably about 1.0 mm, resulting the compacted intermediate in the form of a powder. Optionally a second sieving step is performed, whereas this one should be conducted with a mesh size of 0.3 to 0.5 mm, preferably about 0.5 mm.

Process for Preparing the Intermediate Blends and Final Blends

Intermediate Blends:

Any intermediate blends comprising the API BMW 2992 $MA_2$ in form of a powder are prepared by mixing the API with carrier, binder or combination thereof, glidants, colorants and solid flavours in a freefall or tumble blender.

Final Blends:

Oral Powders:

The intermediate blend comprising BIBW 2992 $MA_2$ in form of a powder is mixed with carriers, binders, glidants, colorants and solid flavours in a freefall or tumble blender.

Oral Granules:

The intermediate blend comprising BIBW 2992 $MA_2$ in form of a powder is mixed with fillers carriers, binders, solid binders, colorants and solid flavours in a freefall or tumble blender. The blend is compacted on a roller compactor and broken up by a granulation-unit with a mesh size of about 2 mm.

Pellets in Capsules:

The intermediate blend comprising BIBW 2992 $MA_2$ in form of a powder is mixed with solid polyethylene glycol and microcrystalline cellulose and extruded through a heated extruder. The pellets are spheronized. After spheronization the resulting pellets are filled in hard gelatin capsules.

Tablets and Filmcoated Tablets:

The intermediate blend comprising BIBW 2992 $MA_2$ in form of a powder is mixed with fillers carriers, binders, glidants and disintegrants in a freefall or tumble blender. Finally the lubricant is added to the main-blend and further mixing is performed.

Process for Preparing the Solid Oral Formulations

Oral Powders:

The final powder blend is filled in sachets.

Oral Granules:

The granules are filled in sachets.

Pellets in capsules:

After spheronization the resulting pellets are filled in hard gelatin capsules.

Tablets and Filmcoated Tablets:

The final blend is compressed on a suitable tablet press to produce tablets by an adequate compression force to obtain the quality parameters with regard to resistance to crushing, tablet height and disintegration as shown in Table 5.

Optionally the tablet cores are coated in a drum-coater by a coating suspension e.g. using a Glatt GC 550/750 coater.

SHORT DESCRIPTION OF THE FIGURES

BIBW 2992 $MA_2$ tablets mentioned in connection with the figures are pharmaceutical dosage forms according to the invention.

FIG. 1 schematically shows the process for preparing the BIBW 2992 $MA_2$ compacted intermediate, comprising (1) a compaction step using roller compaction and a granulation-unit breaking up the ribbons received from the compaction rolls into granules, and (2) a sieving step.

FIG. 2 shows acceleration of disintegration time of 20 mg BIBW 2992 $MA_2$ tablets by increasing roller compaction force.

FIG. 3 shows acceleration of dissolution rate of 20 mg BIBW 2992 $MA_2$ tablets by increasing roller compaction force.

FIG. 4: shows increase of particle size for Compacted Intermediates after dry granulation step of precipitated BIBW 2992 $MA_2$ by variation of Compaction Force measured by Optical Particle Size Analysis.

FIG. 5: shows increase of particle size for Compacted Intermediates after dry granulation step of precipitated BIBW 2992 $MA_2$ by variation of Compaction Force measured by Laser Diffraction Analysis.

FIG. 6: shows the dissolution comparison of BMW 2992 $MA_2$ film-coated tablets in the dosage strengths of 20 mg, 30 mg, 40 mg, 50 mg (as described in Table 4) in 0.1 M hydrochloric acid, pH 1.0; paddle 75 rpm/n=12.

FIG. 7: shows the dissolution comparison of BIBW 2992 $MA_2$ film-coated tablets in the dosage strengths of 20 mg, 30 mg, 40 mg, 50 mg (as described in Table 4) in McIllvaine buffer, pH 4.0; paddle 75 rpm/n=12.

FIG. 8: shows the dissolution comparison of BIBW 2992 $MA_2$ film-coated tablets in the dosage strengths of 20 mg, 30 mg, 40 mg, 50 mg in 0.05 M phosphate buffer, pH 6.8; paddle 75 rpm/n=12.

FIG. 9: shows the dissolution comparison of BIBW 2992 $MA_2$ film-coated tablets 20 mg, 30 mg, 40 mg, 50 mg in water; paddle 50 rpm/n=12.

FIG. 10: shows the individual and geometric mean drug plasma concentration-time profiles of BIBW2992 after multiple oral administration of 40 mg q.d. BIBW 2992 $MA_2$ tablets for 27 days in TP (treatment period) 1 (N=17). The plasma concentration refers to the free base of BIBW2992.

FIG. 11: shows the individual and geometric mean dose normalized maximum plasma concentrations of BIBW 2992 BS after multiple oral administration of BIBW 2992 $MA_2$ tablets at steady state from four Phase I trials.

FIG. 12: shows the individual and geometric mean dose normalized $AUC\tau,ss$ values at steady state of BIBW 2992 BS after multiple oral administration of BIBW 2992 $MA_2$ tablets at steady state from four Phase I trials.

FIG. 13: shows the individual and geometric mean dose normalized maximum plasma concentrations BIBW 2992 BS after multiple oral administration of BIBW 2992 $MA_2$ tablets at day 1 of Treatment Period 1 from one Phase 1 trial.

FIG. 14: shows the individual and geometric mean dose normalized $AUC_{0-24}$ values of BIBW 2992 BS after multiple oral administration of BIBW 2992 $MA_2$ tablets at day 1 of Treatment Period 1 from one Phase I trial.

THE FOLLOWING NON-LIMITING EXAMPLES SERVE TO ILLUSTRATE THE INVENTION

Table 4 shows solid pharmaceutical compositions according to the invention.

TABLE 4

Exemplary composition of solid BIBW 2992 MA$_2$ Tablets

| | Formulation | | | | |
|---|---|---|---|---|---|
| | A | B | C | D | E |
| Ingredient | mg per tablet | mg per tablet | mg per tablet | mg per tablet | mg per tablet |
| BIBW 2992 MA$_2$, unmilled | 29.5600 | 44.3400 | 59.1200 | 73.9000 | 103.4600 |
| (=BIBW 2992 base) | (20.0000) | (30.0000) | (40.0000) | (50.0000) | (70.0000) |
| Lactose monohydrate | 123.8600 | 185.7900 | 247.7200 | 309.6500 | 433.5100 |
| Microcrystalline cellulose | 18.4800 | 27.7200 | 36.9600 | 46.2000 | 64.6800 |
| Crospovidone | 3.6000 | 5.4000 | 7.2000 | 9.0000 | 12.6000 |
| Colloidal anhydrous silica | 0.9000 | 1.3500 | 1.8000 | 2.2500 | 3.1500 |
| Magnesium stearate | 3.6000 | 5.4000 | 7.2000 | 9.0000 | 12.6000 |
| Total | 180.0000 | 270.0000 | 360.0000 | 450.0000 | 630.0000 |

Formulations A, B, C, D and E are tablets which can be coated with a film-coat according to Table 6.

Table 5 shows exemplary properties of solid BMW 2992 MA$_2$ Tablets.

TABLE 5

Exemplary properties of solid BIBW 2992 MA$_2$ Tablets to be obtained by adequate compaction hardness of the tablet press

| Formulation | Tablet Property | Resistance to crushing | Height | Disintegration |
|---|---|---|---|---|
| A | Target | 75N | 3.5 mm | <15 min |
| | Limits of mean | ±20N | n.a. | n.a. |
| | Limits of single | >45N | 3.2-3.8 mm | <20 min |
| B | Target | 90N | 4.1 mm | <15 min |
| | Limits of mean | ±20N | n.a. | n.a. |
| | Limits of single | >65N | 3.8-4.4 mm | <20 min |
| C | Target | 100N | 4.5 mm | <15 min |
| | Limits of mean | ±20N | n.a. | n.a. |
| | Limits of single | >80N | 4.2-4.8 mm | <20 min |
| D | Target | 110N | 5.1 mm | <15 min |
| | Limits of mean | ±20N | n.a. | n.a. |
| | Limits of single | >90N | 4.8-5.4 mm | <20 min |
| E | Target | 125N | 5.9 mm | <15 min |
| | Limits of mean | ±20N | n.a. | n.a. |
| | Limits of single | >95N | 5.6-6.2 mm | <20 min |

TABLE 6

Exemplary composition of Filmcoatings for Formulation A-E

| | Coating for Formulation | | | | |
|---|---|---|---|---|---|
| | A | B | C | D | E |
| Ingredient | mg per tablet | | | | |
| Hypromellose | 2.5000 | 3.5000 | 4.0000 | 5.0000 | 6.0000 |
| Polyethylene glycol 400 | 0.5000 | 0.7000 | 0.8000 | 1.0000 | 1.2000 |
| Titanium dioxid | 1.1300 | 0.6825 | 1.8080 | 0.9750 | 1.1700 |
| Indigo Carmine aluminum lacquer | 0.0700 | 0.2450 | 0.1120 | 0.3500 | 0.4200 |
| Talcum | 0.6500 | 1.6625 | 1.0400 | 2.3750 | 2.8500 |
| Polysorbate 80 | 0.1500 | 0.2100 | 0.2400 | 0.3000 | 0.3600 |
| Purified water (volatile component) | — | — | — | — | — |
| Total | 5.0000 | 7.0000 | 8.0000 | 10.0000 | 12.0000 |

Table 7 shows alternative solid pharmaceutical compositions according to the invention.

TABLE 7

Exemplary composition of solid BIBW 2992 MA$_2$ Tablets

| | Formulation | | | | | |
|---|---|---|---|---|---|---|
| | F | G | H | I | J | K |
| Ingredient | mg per tablet | mg per tablet | mg per tablet | mg per tablet | mg per tablet | mg per tablet |
| BIBW 2992 MA$_2$, unmilled | 7.390 | 29.560 | 147.800 | 7.390 | 29.560 | 147.800 |
| (=BIBW 2992 base) | (5.00) | (20.0000) | (100.0000) | (5.00) | (20.0000) | (100.00) |
| Lactose monohydrate | 58.048 | 232.190 | 550.200 | 65.435 | 261.740 | 616.200 |
| Microcrystalline cellulose | 7.500 | 30.000 | 80.000 | — | — | — |
| Crospovidone | 0.750 | 3.000 | 8.000 | 0.750 | 3.000 | 16.000 |
| Colloidal anhydrous silica | 0.375 | 1.500 | 4.000 | 0.300 | 1.200 | 8.000 |
| Magnesium stearate | 0.937 | 3.750 | 10.000 | 1.125 | 4.500 | 12.000 |
| Total | 75.00 | 300.00 | 800.00 | 75.00 | 300.00 | 800.00 |

Formulations F, G and H are tablets which can be coated with a film-coat according to Table 8.

TABLE 8

Exemplary composition of Filmcoatings for Formulation F-H

| Ingredient | Coating for Formulation | | |
|---|---|---|---|
| | F | G | H |
| | mg per tablet | | |
| Hypromellose | 1.500 | 5.000 | 10.000 |
| Polyethylene glycol 400 | 0.150 | 0.500 | 1.000 |
| Titanium dioxid | 0.750 | 2.500 | 5.000 |
| Talcum | 0.600 | 2.000 | 4.000 |
| Purified water (volatile component) | — | — | — |
| Total | 3.000 | 10.000 | 20.000 |

Table 9 shows alternative pharmaceutical compositions according to the invention. L, M and N are tablets, O can be compressed to form tablets after hot melt-granulation or it can be used as oral granules. Alternatively it can be extruded to pellets and filled into a hard capsule.

TABLE 9

Exemplary composition of Solid BIBW 2992 MA$_2$ Formulations

| Formulation | L | M | N | O | P | Q |
|---|---|---|---|---|---|---|
| BIBW 2992 MA$_2$ Compacted Intermediate | 60.0 mg | 30.0 mg | 30.0 mg | 30.0 mg | 30.0 mg | 30.0 mg |
| Lactose monohydrate | 42.5 mg | 125.0 mg | — | — | — | 125.0 mg |
| Microcrystalline cellulose | — | 20.0 mg | 125.0 mg | 70.0 mg | — | 20.0 mg |
| Calcium phopsphate | 40.5 mg | — | 20.0 mg | — | — | — |
| Soybean Oil | — | — | — | — | 145.0 mg | — |
| Macrogol 6000 | — | — | — | 80.0 mg | — | — |
| Copovidone | 2.0 mg | — | — | — | — | — |
| Sodium starch glycolate | 5.0 mg | — | — | — | — | — |
| Crospovidone | — | 5.0 mg | 5.0 mg | — | — | 5.0 mg |
| Colloidal silica | 1.0 mg | 1.0 mg | 1.0 mg | — | 10.0 | 1.0 mg |
| Solid flavour | — | — | — | 5.0 mg | — | 4.0 mg |
| Magnesium stearate | 4.0 mg | 4.0 mg | 4.0 mg | — | — | — |
| Total | 185.0 mg | 185.0 mg | 185.0 mg | 185.0 mg | 185.0 mg | 185.0 mg |

Formulation P is prepared as a liquid fillmix of suspended compacted intermediate of BMW 2992 MA$_2$. After homogenization it is filled either in hard or soft gelatin capsules. Formulation Q is an oral powder.

The invention claimed is:

1. A compacted intermediate consisting of BIBW 2992 MA$_2$ (API salt) and an amount of 0 to 1.0% of a lubricant, calculated on the amount of API salt by weight, in form of a powder with a particle size distribution of x10<200 μm, 1 μm<x50<300 μm, 75 μm<x90<600 μm, obtainable by roller compaction, combined with at least one sieving step after compaction.

2. The compacted intermediate of claim 1 characterized by a poured density ($\rho_p$) in the range of 0.2 g/mL<$\rho_p$<1.0 g/mL and/or a Hausner Factor (HF) in the range of 1.00<HF<1.30.

3. An intermediate or final blend prepared from the compacted intermediate according to claim 1.

4. The intermediate or final blend according to claim 3, further characterized by contents selected from components (a) to (g):
  (a) compacted intermediate of BIBW 2992 MA$_2$ in an amount of about 1 to 99% by weight,
  (b) optionally one or more carriers in an amount of about 10 to 99% by weight,
  (c) one or more binders in an amount of about 0 to 99% by weight,
  (d) one or more glidants in an amount of about 0 to 10% by weight,
  (e) one or more disintegrants in an amount of about 0 to 10% by weight,
  (f) one or more lubricants in an amount of about 0 to 10% by weight, and
  (g) 0 to 10% by weight of further excipients and/or adjuvants, wherein presence of at least one of components (b) to (g) is mandatory but also two up to at most all six of the optional components (b) to (g) are allowed to be present in addition to component (a) in the intermediate and final blend, the sum of all components adding to 100%.

5. A solid oral formulation ready for use/ingestion prepared from the compacted intermediate of BIBW 2992 MA$_2$ according to claim 1.

6. The solid oral formulation according to claim 5 selected from powders, granules, pellets, tablets, capsules, chewable tablets, dispersible tablets, troches and lozenges.

7. A solid oral formulation, wherein the formulation is a tablet and obtained by direct compression of a final blend according to claim 3 or by tableting of pellets or granules obtained by conventional wet-, dry or hot-melt granulation of an intermediate blend according to claim 3.

8. The tablet of claim 7, said tablet being uncoated or coated.

9. The tablet of claim 8, comprising 1 to 150 mg of the API, based on BIBW 2992 (the free base).

10. The tablet of claim 9, further comprising
50 to 500 mg of carrier, binder or a combination thereof,
0.1 to 5 mg of a glidant,
1 to 15 mg of a disintegrant, and
1 to 15 mg of a lubricant.

11. The solid formulation of claim 5, packaged in PVC-blisters, PVDC-blisters or a moisture-proof packaging material such as aluminium foil blister packs, alu/alu blister, transparent or opaque polymer blister with pouch, polypropylene tubes, colored blister materials, tubes, brown glass bottles glass bottles and HDPE bottles optionally containing a child-resistant feature, optionally comprising a desiccant such as molecular sieve or silica gel.

12. A method for producing the compacted intermediate of BIBW 2992 MA$_2$ according to claim 1 in form of a powder comprising compacting by roller compaction combined with at least one sieving step.

13. The method of claim 12, wherein the roller compaction step is carried out with
BIBW 2992 MA$_2$ alone or, optionally, with
a pre-blend of BIBW 2992 MA$_2$ with 0 to 1.0% of a lubricant in a freefall or tumble blender to prevent major sticking on the compaction rolls.

14. The method of claim 13, wherein the roller compaction step is carried out on a roller compactor
optionally with horizontally, vertically or 45° angle alignment of the compaction rolls,
which may be smooth or shaped on their surface;
using a compaction force varying
between 1 kN/cm and 20 kN/cm,
at a compaction speed of the compaction rolls
between 1 rpm and 30 rpm,
and a gap width between the compaction rolls
between 1 mm and 10 mm.

15. A solid oral formulation ready for use/ingestion prepared from an intermediate blend according to claim 3.

16. The solid oral formulation according to claim 15 selected from powders, granules, pellets, tablets, capsules, troches and lozenges.

17. The solid formulation of claim 15, packaged in PVC-blisters, PVDC-blisters or a moisture-proof packaging material such as aluminium foil blister packs, alu/alu blister, transparent or opaque polymer blister with pouch, polypropylene tubes, colored blister materials, tubes, brown glass bottles glass bottles and HDPE bottles optionally containing a child-resistant feature, optionally comprising a desiccant such as molecular sieve or silica gel.

18. The solid oral formulation according to claim 16 which is in the form of a tablet selected from chewable tablet and dispersible tablet.

19. The tablet of claim 18, characterized by a composition selected from formulations A, B, C, D and E:

|  | Formulation | | | | |
| --- | --- | --- | --- | --- | --- |
|  | A | B | C | D | E |
| Ingredient | mg per tablet | mg per tablet | mg per tablet | mg per tablet | mg per tablet |
| BIBW 2992 MA$_2$, unmilled | 29.5600 | 44.3400 | 59.1200 | 73.9000 | 103.4600 |
| (=BIBW 2992 base) | (20.0000) | (30.0000) | (40.0000) | (50.0000) | (70.0000) |
| Lactose monohydrate | 123.8600 | 185.7900 | 247.7200 | 309.6500 | 433.5100 |
| Microcrystalline cellulose | 18.4800 | 27.7200 | 36.9600 | 46.2000 | 64.6800 |
| Crospovidone | 3.6000 | 5.4000 | 7.2000 | 9.0000 | 12.6000 |
| Colloidal anhydrous silica | 0.9000 | 1.3500 | 1.8000 | 2.2500 | 3.1500 |
| Magnesium stearate | 3.6000 | 5.4000 | 7.2000 | 9.0000 | 12.6000 |
| Total | 180.0000 | 270.0000 | 360.0000 | 450.0000 | 630.0000 | which optionally are coated with a film-coat characterized by the following compositions selected for formulations A, B, C, D and E:

|  | Coating for Formulation | | | | |
| --- | --- | --- | --- | --- | --- |
|  | A | B | C | D | E |
| Ingredient | mg per tablet | | | | |
| Hypromellose | 2.5000 | 3.5000 | 4.0000 | 5.0000 | 6.0000 |
| Polyethylene glycol 400 | 0.5000 | 0.7000 | 0.8000 | 1.0000 | 1.2000 |
| Titanium dioxid | 1.1300 | 0.6825 | 1.8080 | 0.9750 | 1.1700 |
| Indigo Carmine aluminum lacquer | 0.0700 | 0.2450 | 0.1120 | 0.3500 | 0.4200 |
| Talcum | 0.6500 | 1.6625 | 1.0400 | 2.3750 | 2.8500 |
| Polysorbate 80 | 0.1500 | 0.2100 | 0.2400 | 0.3000 | 0.3600 |
| Purified water (volatile component) | — | — | — | — | — |
| Total | 5.0000 | 7.0000 | 8.0000 | 10.0000 | 12.0000. |

20. The tablet of claim 18, characterized by a composition selected from formulations F, G, H, I, J and K:

|  | Formulation | | | | | |
|---|---|---|---|---|---|---|
| Ingredient | F mg per tablet | G mg per tablet | H mg per tablet | I mg per tablet | J mg per tablet | K mg per tablet |
| BIBW 2992 MA$_2$, unmilled (=BIBW 2992 base) | 7.390 (5.00) | 29.560 (20.0000) | 147.800 (100.0000) | 7.390 (5.00) | 29.560 (20.0000) | 147.800 (100.00) |
| Lactose monohydrate | 58.048 | 232.190 | 550.200 | 65.435 | 261.740 | 616.200 |
| Microcrystalline cellulose | 7.500 | 30.000 | 80.000 | — | — | — |
| Crospovidone | 0.750 | 3.000 | 8.000 | 0.750 | 3.000 | 16.000 |
| Colloidal anhydrous silica | 0.375 | 1.500 | 4.000 | 0.300 | 1.200 | 8.000 |
| Magnesium stearate | 0.937 | 3.750 | 10.000 | 1.125 | 4.500 | 12.000 |
| Total | 75.00 | 300.00 | 800.00 | 75.00 | 300.00 | 800.00 | formulations F, G and H optionally being coated with a film-coat characterized by the following compositions:

| | Coating for Formulation | | |
|---|---|---|---|
| Ingredient | F | G | H |
| | mg per tablet | | |
| Hypromellose | 1.500 | 5.000 | 10.000 |
| Polyethylene glycol 400 | 0.150 | 0.500 | 1.000 |
| Titanium dioxid | 0.750 | 2.500 | 5.000 |
| Talcum | 0.600 | 2.000 | 4.000 |
| Purified water (volatile component) | — | — | — |
| Total | 3.000 | 10.000 | 20.000. |

* * * * *

UNITED STATES PATENT AND TRADEMARK OFFICE
CERTIFICATE OF CORRECTION

PATENT NO.         : 8,545,884 B2                                         Page 1 of 1
APPLICATION NO.    : 12/995715
DATED              : October 1, 2013
INVENTOR(S)        : Messerschmid et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 227 days.

Signed and Sealed this
Fifteenth Day of September, 2015

Michelle K. Lee
*Director of the United States Patent and Trademark Office*